US007570364B2

(12) United States Patent
Kuroiwa

(10) Patent No.: US 7,570,364 B2
(45) Date of Patent: Aug. 4, 2009

(54) OPTICAL TOMOGRAPHIC IMAGING APPARATUS

(75) Inventor: Karin Kuroiwa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 63 days.

(21) Appl. No.: 11/951,643

(22) Filed: Dec. 6, 2007

(65) Prior Publication Data
US 2008/0140328 A1      Jun. 12, 2008

(30) Foreign Application Priority Data
Dec. 7, 2006      (JP)      ................ 2006-330877

(51) Int. Cl.
*G01B 11/02*      (2006.01)
(52) U.S. Cl. ....................... 356/479; 356/497
(58) Field of Classification Search ............. 356/477, 356/479, 497
See application file for complete search history.

(56) References Cited

U.S. PATENT DOCUMENTS

| 6,665,320 | B1 | 12/2003 | Arbore et al. | |
| 7,324,211 | B2* | 1/2008 | Tsujita | 356/497 |
| 7,355,716 | B2* | 4/2008 | de Boer et al. | 356/479 |
| 7,359,062 | B2* | 4/2008 | Chen et al. | 356/479 |
| 2006/0066865 | A1* | 3/2006 | Tsujita | 356/479 |
| 2006/0244973 | A1* | 11/2006 | Yun et al. | 356/511 |
| 2008/0117424 | A1* | 5/2008 | Teramura et al. | 356/450 |
| 2008/0117427 | A1* | 5/2008 | Teramura et al. | 356/484 |
| 2008/0117431 | A1* | 5/2008 | Teramura | 356/511 |
| 2008/0137094 | A1* | 6/2008 | Teramura et al. | 356/489 |
| 2008/0140325 | A1* | 6/2008 | Teramura | 702/57 |
| 2008/0140328 | A1* | 6/2008 | Kuroiwa | 702/66 |
| 2009/0036782 | A1* | 2/2009 | Vakoc et al. | 600/476 |

FOREIGN PATENT DOCUMENTS

| JP | 2001264246 A | 9/2001 |
| JP | 2002214125 A | 7/2002 |
| JP | 2006047264 A | 2/2006 |

OTHER PUBLICATIONS

M. Takeda et al., "Optical Frequency Scanning Interference Microscopes", Optical Engineering Contact, 2003, pp. 426-432, vol. 41, No. 7 and its partial translation.

* cited by examiner

*Primary Examiner*—Patrick J Connolly
(74) *Attorney, Agent, or Firm*—Sughrue Mion, PLLC

(57) ABSTRACT

Light beams swept in wavelength repeatedly within first and second wavelength ranges respectively are outputted from a light source unit at the same time. Each light beam is split into measuring and reference beams. Reflected beams from a measuring object when the measuring beams are irradiated on the measuring object are combined with the reference beams. The wavelengths of the interference beams produced thereby are divided into three wavelength ranges, for example, a range not greater than 0.9 μm, a range from 0.9 to 1.2 μm, and a range longer than 1.2 μm by a wavelength dividing means to obtain interference signals. In the wavelength range from 0.9 to 1.2 μm which includes an overlapping wavelength range where the wavelength ranges of the light beams overlap with each other, either one of the light beams is outputted from the light source unit.

8 Claims, 14 Drawing Sheets

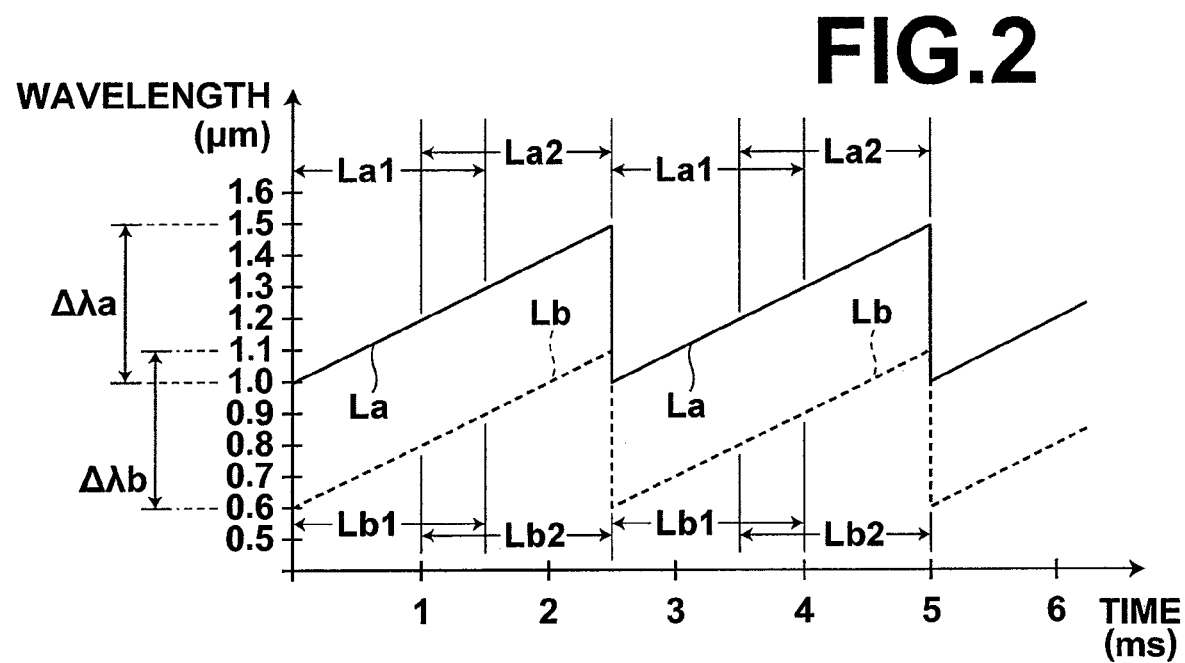

FIG.8
INTERMEDIATE REFLECTED INTENSITY $r_a$
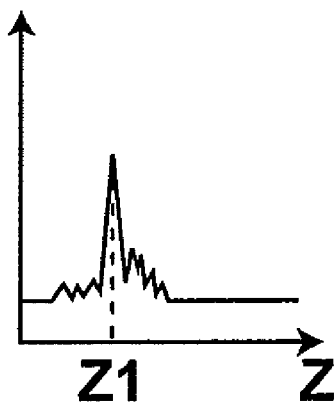
INTERMEDIATE REFLECTED INTENSITY $r_b$
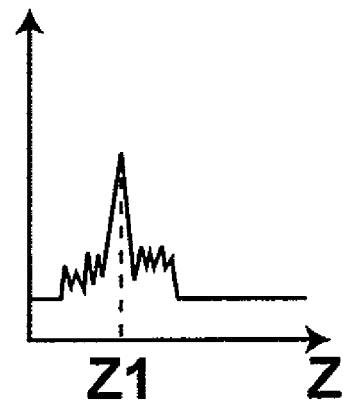
INTERMEDIATE REFLECTED INTENSITY $r$
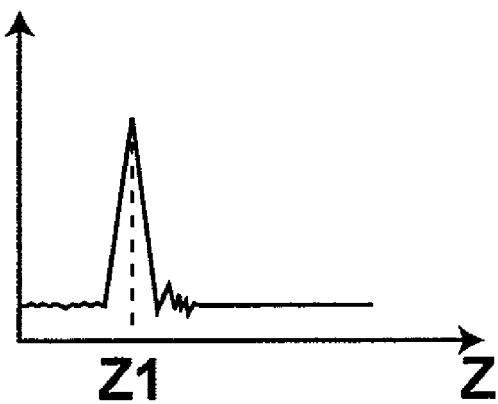

OPTICAL TOMOGRAPHIC IMAGING APPARATUS

BACKGROUND OF THE INVENTION

Field of the Invention

The present invention relates to an optical tomographic imaging apparatus for obtaining a tomographic image of a measuring object by OCT (optical coherence tomography) measurement.

An optical tomographic image obtaining system using OCT measurement is sometimes used to obtain an optical tomographic image of a living tissue. In the optical tomographic image obtaining system, a low coherence light beam outputted from the light source is split into measuring and reference beams, and the measuring beam is irradiated onto a measuring object, then the reflected beam from the measuring object or backscattered light when the measuring beam is irradiated thereon is combined with the reference beam, and an optical tomographic image is obtained based on the intensity of the interference beam between the reflected beam and the reference beam. Hereinafter, reflected beam from a measuring object and backscattered light are collectively referred to as the "reflected beam".

The OCT measurement is largely categorized into TD-OCT (Time Domain OCT) measurement and FD (Fourier Domain)-OCT measurement. The TD-OCT measurement is a method for obtaining a reflected beam intensity distribution corresponding to a position in the depth direction (depth position) of a measuring object by measuring interference beam intensity while changing the optical path length of the reference light.

The FD-OCT measurement is a method for obtaining a reflected light intensity distribution corresponding to a depth position of a measuring object by measuring interference beam intensity with respect to each spectral component of the beam without changing the optical path length of the reference beam, and performing frequency analysis, typically a Fourier transform, on the obtained spectral interference intensity signals using a computer. The FD-OCT does not require the mechanical scanning used in TD-OCT, so that it has been drawing wide attention as a method that allows high speed measurement.

Typical systems that use FD-OCT measurement are SD-OCT (Spectral Domain OCT) system and SS-OCT (Swept Source OCT) system. The SD-OCT system uses a broadband and low coherence light beam, such as SLD (Super Luminescence Diode), ASE (Amplified Spontaneous Emission), or white light beam, as the light source, and forms an optical tomographic image in the following manner. The broadband and low coherence light beam is split into measuring and reference beams using Michelson interferometer or the like and the measuring beam is irradiated onto a measuring object, then a reflected beam from the measuring object when the measuring beam is irradiated thereon is caused to interfere with the reference beam and the interference beam is broken down into frequency components using a spectroscopic device, thereafter the intensity of the interference beam with respect to each frequency component is measured using a detector array including elements, such as photodiodes, disposed in an array and an optical tomographic image is formed by performing Fourier transform on the obtained spectral interference signals using a computer.

In the mean time, the SS-OCT system uses a laser that temporally sweeps the optical frequency, in which the reflected beam is caused to interfere with the reference beam at each wavelength, then the temporal waveform of the signal corresponding to the temporal change in the optical frequency is measured and an optical tomographic image is formed by performing Fourier transform on the obtained spectral interference signals using a computer.

For the OCT system, in order to obtain a high resolution and high quality image, it is necessary to broaden the wavelength range of the light source and to increase the number of corresponding data points. In the SD-OCT system, however, the interference beams are generally detected with respect to each wavelength using a detector array including elements, such as photodiodes, disposed in an array, so that the number of data points is limited by the number of elements of the detector array. At present, it is not desirable to increase the number of elements of the detector array for increasing the number of data points, since such increase would result in cost increase, decreased manufacturability, reduced measuring rate, and the like. On the other hand, in the SS-OCT system, in order to increase the number of data points, for example, it is just necessary to increase the sampling frequency of the circuit that converts an optical current signal from the detector to a digital value if the frequency sweep period of the light source is assumed to be constant, so that it may be realized easily at low cost with a high measuring rate.

In various types of OCT measurements described above, it is known that the measuring beam with a broad spectral width is used in order to improve spatial resolution as described, for example, in Japanese Unexamined Patent Publication No. 2002-214125. This patent publication discloses a light source including a plurality of light sources, each emitting a light beam having a different spectral range, and an optical coupler for combining the light beams emitted from the respective light sources to emit a single-wave light beam as a light source capable of emitting a light beam having a broad spectral width.

For the SD-OCT measurement, a method for forming a continuous spectrum by combining light beams from a plurality of gain media, each having a overlapping wavelength range with each other, is disclosed in Japanese Unexamined Patent Publication No. 2001-264246. As for the method of forming a continuous spectrum through wavelength combination for SS-OCT, a structure including a plurality of wavelength scanning light sources, each having a gain medium and a wavelength selection element is disclosed in Japanese Unexamined Patent Publication No. 2006-047264. Further, U.S. Pat. No. 6,665,320 discloses a structure that simultaneously controls light beams from a plurality of gain media using a single wavelength selection element.

Where light beams from a plurality of light sources are combined and used in order to obtain high spatial resolution, the conventional SS-OCT system poses a problem that, when light beams having different wavelengths are outputted from a plurality of light sources and irradiated onto a measuring object at the same time, the interference information provided by the plurality of light beams is mixed up and unable to be detected since the detector of the system includes only a single element.

For this reason, in the systems described in Japanese Unexamined Patent Publication No. 2006-047264, and U.S. Pat. No. 6,665,320, a configuration is adopted in which only a single wavelength is inputted to the detector at a time by controlling the light source or using a switching element. Such method, however, poses a problem that the measuring rate is reduced since it takes time to irradiate all of the wavelengths of the measuring beam, though it may provide a broadband beam as the measuring beam.

The present invention has been developed in view of the circumstances described above, and it is an object of the present invention to provide an optical tomographic imaging apparatus capable of rapidly obtaining a high resolution tomographic image.

SUMMARY OF THE INVENTION

An optical tomographic imaging apparatus of the present invention includes:

a light source unit having a first light source that outputs a first light beam which is swept in wavelength repeatedly within a first wavelength range, and a second light source that outputs a second light beam which is swept in wavelength repeatedly within a second wavelength range which is different in range from the first wavelength range, in which a part of the wavelength sweep of the first light beam and a part of the wavelength sweep of the second light beam are performed at the same time;

a beam splitting means that splits the first and second light beams into first measuring and reference beams, and second measuring and reference beams respectively;

a beam combining means that combines first and second reflected beams, which are the reflected beams from a measuring object when the first and second measuring beams are irradiated on the measuring object, with the first and second reference beams respectively;

a wavelength dividing means that divides a first interference beam produced when the first reflected beam is combined with the first reference beam by the beam combining means and a second interference beam produced when the second reflected beam is combined with the second reference beam by the beam combining means into at least a third wavelength range which includes a portion of the first wavelength range and a portion of the second wavelength range, a fourth wavelength range which is shifted on the short wavelength side of the third wavelength range, and a fifth wavelength range which is shifted on the long wavelength side of the third wavelength range;

a first interference beam detection means that detects an interference beam within the third wavelength range as a first interference signal, a second interference beam detection means that detects an interference beam within the fourth wavelength range as a second interference signal, and a third interference beam detection means that detects an interference beam within the fifth wavelength range as a third interference signal; and a tomographic image processing means that generates a tomographic image of the measuring object using the first, second, and third interference signals detected by the first, second, and third interference beam detection means respectively.

Each of the first and second light sources may be structured in any manner as long as capable of outputting a light beam which is swept in wavelength repeatedly within a predetermined wavelength range. For example, it may be formed of a single wavelength swept laser or a plurality of wavelength swept lasers as long as the light beam outputted therefrom may be regarded as substantially identical to the light beam outputted from a single wavelength swept laser.

The referent of "reflected beams from a measuring object" as used herein means to include light beams scattered by the measuring object in addition to light beams reflected from the measuring object.

If the first and second wavelength ranges include an overlapping wavelength range where the wavelength ranges overlap with each other at an end portion thereof on either the long wavelength side or the short wavelength side, and the third wavelength range includes the entire portion of the overlapping wavelength range, then while a light beam with a wavelength within the third wavelength range is outputted from either one of the first and second light sources, light beams with wavelengths within the third wavelength range may be outputted only from the either one of the light sources.

The wavelength dividing means may be anything as long as capable of dividing a wavelength. For example, it may be formed of a WDM (Wavelength Division Multiplexing) coupler or two dichroic mirrors.

If the apparatus includes a frequency versus time characteristic detection means that detects a frequency versus time characteristic of each of the first and second light beams and outputs to the tomographic image processing means, the tomographic image processing means may be a means that generates the tomographic image using the frequency versus time characteristic of each of the first and second light beams detected by the frequency versus time characteristic detection means.

According to the optical tomographic imaging apparatus of the present invention, a first interference beam produced when the first reflected beam is combined with the first reference beam by the beam combining means, and a second interference beam produced when the second reflected beam is combined with the second reference beam by the beam combining means are divided into at least a third wavelength range which includes a portion of the first wavelength range and a portion of the second wavelength range, a fourth wavelength range which is shifted on the short wavelength side of the third wavelength range, and a fifth wavelength range which is shifted on the long wavelength side of the third wavelength range. Then, an interference beam within the third wavelength range is detected as a first interference signal, an interference beam within the fourth wavelength range is detected as a second interference signal, and an interference beam within the fifth wavelength range is detected as a third interference signal, and a tomographic image is generated based on these interference signals. Accordingly, even if the first and second light beams having wavelength ranges partly overlapping with each other or end portions thereof are in close proximity to each other are irradiated on a measuring object at the same time, interference signals corresponding to interference beams within the wavelength ranges partly overlapping with each other or end portions thereof are in close proximity to each other may be obtained, since the interference signals are obtained by dividing the first and second interference beams produced at that time into three wavelength ranges. This may improve the measuring rate in comparison with the past, so that a higher resolution tomographic image may be obtained more rapidly.

Further, if the first and second wavelength ranges include an overlapping wavelength range where the wavelength ranges overlap with each other at an end portion thereof on either the long wavelength side or the short wavelength side, and the third wavelength range includes the entire portion of the overlapping wavelength range, then while a light beam with a wavelength within the third wavelength range is outputted from either one of the first and second light sources, light beams with wavelengths within the third wavelength range are outputted only from the either one of the light sources. Accordingly, even if the first and second light beams are irradiated on a measuring object at the same time, the interference signal generated by the first interference beam and the interference signal generated by the second interference beam at that time are not mixed together, so that the interference signal generated by the first interference beam and the interference signal generated by the second interference beam may be obtained at the same time. This may improve the measuring rate in comparison with the past, so that a higher resolution tomographic image may be obtained more rapidly.

In a conventional tomographic imaging apparatus having a plurality of light sources or a plurality of gain media, synchronization control is required such that only a single wavelength is inputted to the detector. But the tomographic imaging apparatus of the present invention does not require such control, so that the apparatus may be simplified. Further, in the tomographic imaging apparatus of the present invention, each of the interference beam detection means may be structured optimally according to the wavelength ranges of the divided wavelengths, so that detection accuracy of each of the interference beam detection means may be improved and the resolution of a tomographic image to be obtained may be increased. Still further, components and parts used in the interference beam detection means need only to cover each wavelength range of divided wavelength, not to cover a broadband light beam. This may relax the restrictions on the components and parts to be used in comparison with the past and allow the use of general purpose components and parts, so that the apparatus may be constructed easily.

BRIEF DESCRIPTION OF THE DRAWINGS

FIG. 2 illustrates wavelength sweep of the light source unit shown in FIG. 1.

FIG. 8 illustrates how the reflected intensity used for generating a tomographic image is generated from a plurality of reflected intensities in the tomographic image processing means shown in FIG. 1.

DESCRIPTION OF THE PREFERRED EMBODIMENTS

Figure 1:
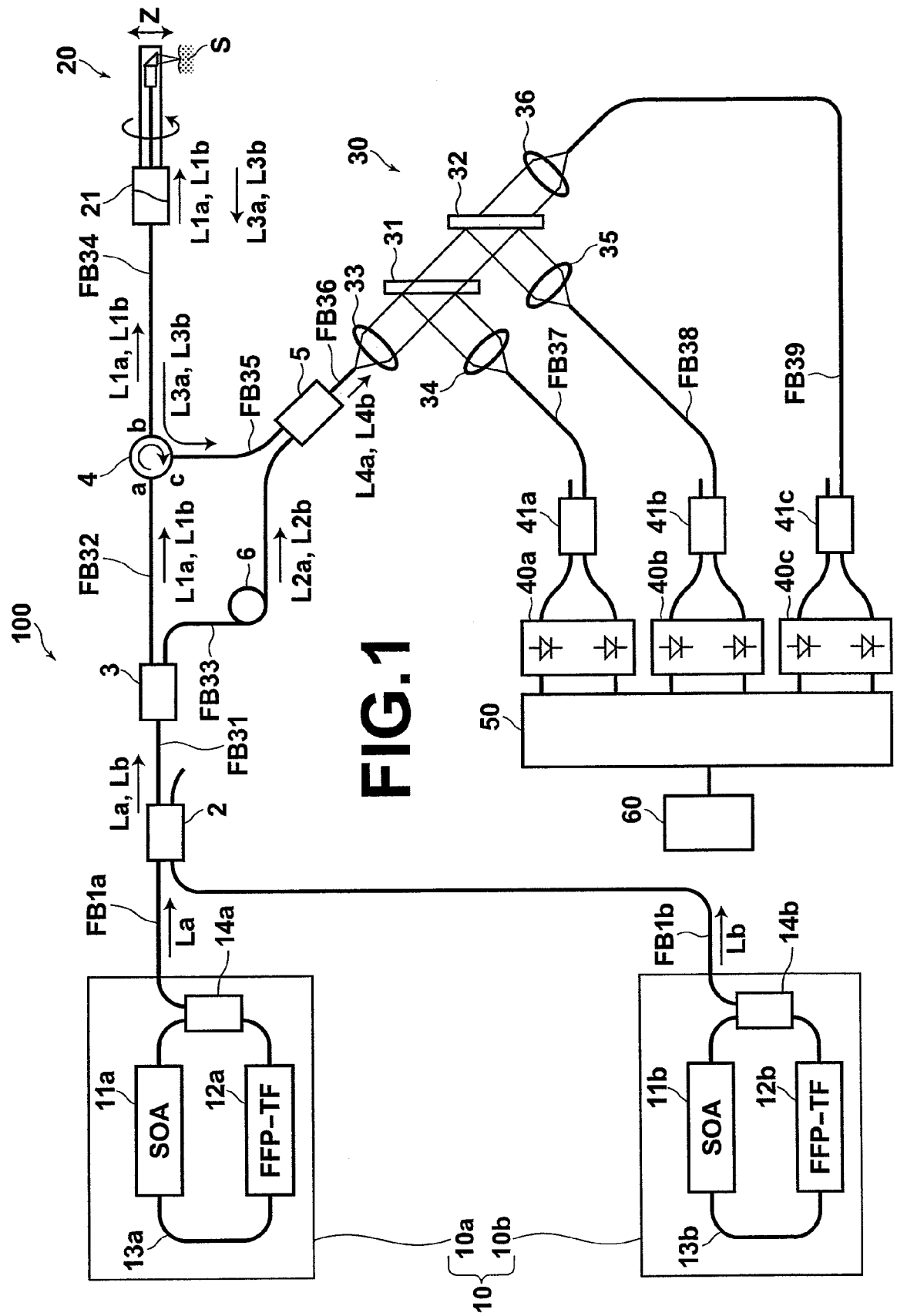
FIG. 1 is a schematic configuration diagram of the optical tomographic imaging apparatus according to a first embodiment of the present invention.

Hereinafter, embodiments of the optical tomographic imaging apparatus of the present invention will be described in detail with reference to the accompanying drawings. FIG. 1 is a schematic configuration diagram of the optical tomographic imaging apparatus 100 according to a first embodiment of the present invention. The optical tomographic imaging apparatus 100 is, for example, an apparatus for obtaining a tomographic image of a measuring object such as a living tissue or a cell in a body cavity by the aforementioned SS-OCT measurement using a Mach-Zehnder interferometer.

The optical tomographic imaging apparatus 100 includes: a light source unit 10 having a light source 10a that outputs a light beam La which is swept in wavelength within a wavelength range $\Delta\lambda a$ (1.0 to 1.5 μm) at a constant period and a light source 10b that outputs a light beam Lb which is swept in wavelength within a wavelength range $\Delta\lambda b$ (0.6 to 1.1 μm) at a constant period; a beam combining means 2 that combines the light beams La and Lb outputted from the light source unit 10; a beam splitting means 3 that splits the light beam La into a measuring beam L1a and a reference beam L2a, and the light beam Lb into a measuring beam L1b and a reference beam L2b; and a circulator 4 that outputs the measuring beams L1a and L1b inputted from port "a" to port "b", and outputs reflected beams L3a and L3b inputted from port "b" to port "c". The apparatus 100 further includes: a beam combining means 5 that combines the reflected beam L3a with the reference beam L2a, and the reflected beam L3b with the reference beam L2b; a wavelength dividing means 30 that divides the wavelength of an interference beam L4a produced when the reflected beam L3a is combined with the reference beam L2a, and the wavelength of an interference beam L4b produced when the reflected beam L3b is combined with the reference beam L2b into three wavelength ranges: a range not longer than 0.9 μm, a range from over 0.9 to 1.2 μm, and a range longer than 1.2 μm; interference beam detection means 40a, 40b, and 40c that detect the interference beams in the respective wavelength ranges as interference signals; and a tomographic image processing means 50 that obtains a tomographic image of a measuring object S using the interference signals detected by the interference beam detection means 40a, 40b, and 40c.

It is noted that the measuring beam L1a, reference beam L2a, reflected beam L3a, and interference beam L4a are the light beams based on the light beam La and in the same wavelength range as that of the light beam La. Likewise, the measuring beam L1b, reference beam L2b, reflected beam L3a, and interference beam L4a are the light beams based on the light beam Lb and in the same wavelength range as that of the light beam Lb.

The light source 10a of the light source unit 10 includes, as the major components, a semiconductor optical amplifier (SOA) 11a as a gain medium, a wavelength selection means 12a constituted by a fiber Fabry-Perot tunable filter (FFP-TF), and an optical fiber 13a connected to both ends of the semiconductor optical amplifier 11a and wavelength selection means 12a for forming a ring-shaped resonator.

The semiconductor optical amplifier 11a has functions, through injection of drive current therein, to output a weak emission light beam to an optical fiber 13a connected to one end thereof and to amplify a light beam inputted from the optical fiber 13a connected to the other end thereof. By the semiconductor optical amplifier 11a, the laser beam is oscillated in the ring-shaped resonator, which is branched by an optical coupler 14a with a branching ratio of 10:90 connected to the optical fiber 13a, then guided through an optical fiber FB1a, and outputted to outside as the light beam La.

The wavelength selection means 12a is constructed such that the wavelength of the light beam to be transmitted is changeable, which allows the wavelength of the laser beam oscillating in the ring-shaped resonator to be selectable, so that the wavelength may be swept at a constant period.

The light source 10b is structured in the same manner as the light source 10a, and includes as the major components: a semiconductor optical amplifier 11b as a gain medium; a wavelength selection means 12b constituted by a FFP-TP; and an optical fiber 13b connected to both ends of the SOA 11b and FFP-TP 12b for forming a ring-shaped resonator. The laser beam oscillating in the resonator of the light source 10b is branched by an optical coupler 14b with a branching ratio of 10:90 connected to the optical fiber 13b, then guided through an optical fiber FB1b, and outputted to outside as the light beam Lb. In the light source 10b, wavelength selection is also performed by the wavelength selection means 12b, so that the wavelength may be swept at a constant period.

FIG. 2 shows wavelength sweep of the light beams La and Lb outputted from the light sources 10a and 10b respectively, illustrating the relationship between time and wavelength. As illustrated in FIG. 2, the light source 10a sweeps the wavelength within the wavelength range $\Delta\lambda a$ (1.0 to 1.5 µm) at a period of, for example, 2.5 ms, and the light source 10b sweeps the wavelength within the wavelength range $\Delta\lambda b$ (0.6 to 1.1 µm) at a period of 2.5 ms simultaneously with the light source 10a.

The light beam La propagated through the optical fiber FB1a and the light beam Lb propagated through the optical fiber FB1b are combined by the beam combining means 2, and outputted to an optical fiber FB31, which propagates through the optical fiber FB31 and inputted to the beam splitting means 3.

The beam splitting means 3 includes, for example, a 2×2 optical coupler with a branching ratio of 90:10. The beam splitting means 3 splits the light beam La into the measuring beam L1a and reference beam L2a, and the light beam Lb into the measuring beam L1b and reference beam L2b. Here, the beam splitting means 3 splits the respective light beams into the respective measuring and reference beams at a ratio of 90:10. The measuring beams L1a and L1b are outputted to an optical fiber FB32, and the reference beams L2a and L2b are outputted to an optical fiber FB33.

The circulator 4 is provided in the optical path between the light splitting means 3 and a probe 20, and the measuring beams L1a and L1b inputted from the port "a" on the side of the beam splitting means 3 are outputted to an optical fiber FB34 from the port "b" on the side of the probe 20.

The probe 20 guides the measuring beams L1a and L1b inputted through an optical rotary connector 21 to the measuring object S, and the measuring beams L1a and L1b are irradiated on the same position of the measuring object S at the same time. The probe 20 also guides the reflected beams L3a and L3b from the measuring object S when the measuring beams L1a and L1b are irradiated onto the measuring object S. The probe 20 is structured such that the fiber section at the distal side of the optical rotary connector 31 is rotated by a not shown motor to circularly scan the beams on the sample, which enables a two dimensional tomographic image measurement. Further, a three dimensional tomographic image measurement is feasible by scanning the tip of the probe 20 by a not shown motor in the direction orthogonal to the plane formed by the scan circle of the light path. The probe 20 is detachably attached to the optical fiber FB 34 through a not shown optical connector. It should be appreciated that the shape of the probe tip and the scanning direction are not limited to those described above. For example, the two dimensional scanning may be performed by providing a high speed scanning mirror at the distal end of the fiber.

The reflected beams L3a and L3b outputted from the probe 20 through the optical fiber FB34 are inputted to the port "b" of the circulator 4, and outputted to an optical fiber FB35 from the port "c". In the beam combining means 5, the reflected beams L3a and L3b are combined with the reference beams L2a and L2b respectively, and interference beams L4a and L4b are outputted to an optical fiber FB36. A transmission type optical path length control means 6 is provided in the optical path of the reference beams L2a and L2b between the beam splitting means 3 and beam combining means 5. The optical path length control means 6 changes the optical path length of the reference beams L2a and L2b to control the starting position for obtaining a tomographic image.

Figure 3A:
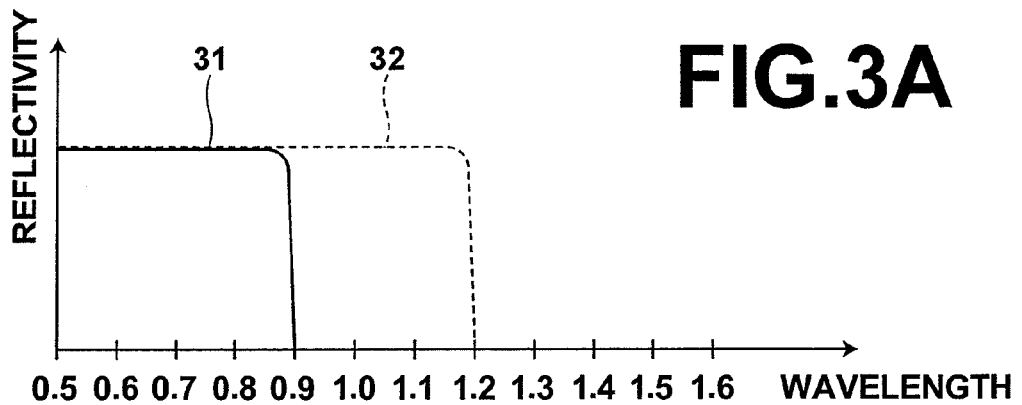
FIGS. 3A to 3D illustrate wavelength reflection characteristic of the dichroic mirror.
Figure 3B:
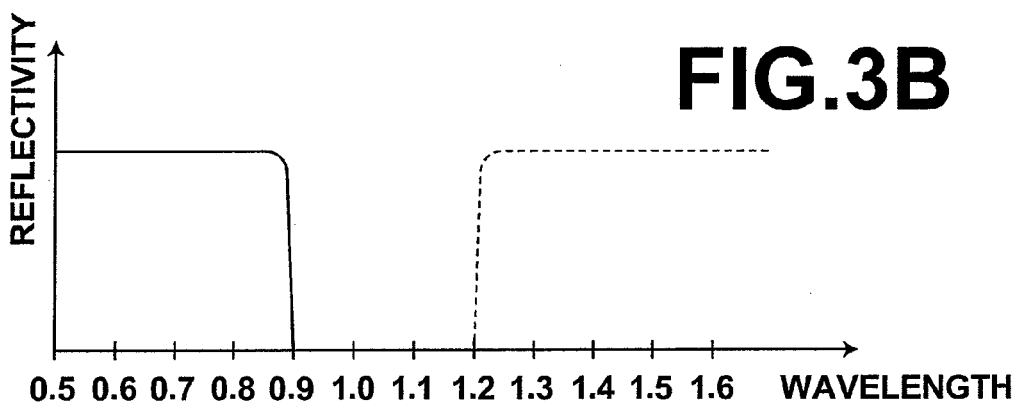

The wavelength dividing means 30 has a function to divide light according to a determined wavelength and includes: a dichroic mirror 31 that reflects light beams with wavelengths not longer than 0.9 µm and transmits light beams with wavelengths longer than 0.9 µm; a dichroic mirror 32 that reflects light beams with wavelengths not longer than 1.2 µm and transmits light beams with wavelengths longer than 1.2 µm; and lenses 33 to 36. Interference beams with wavelengths not longer than 0.9 µm (interference beams within a fourth wavelength range of the present invention) within the interference beams L4a and L4b are inputted to an optical fiber FB37, interference beams with wavelengths longer than 0.9 µm and not longer than 1.2 µm (interference beams within a third wavelength range of the present invention) are inputted to an optical fiber FB38, and interference beams with wavelengths longer than 1.2 µm (interference beams within a fifth wavelength range of the present invention) are inputted to an optical fiber FB39. The wavelength reflection characteristic of the dichroic mirrors 31 and 32 are shown in FIG. 3A. It is noted that a dichroic mirror that transmits light beams with wavelengths not longer than 1.2 µm and reflects light beams with wavelength longer than 1.2 µm may be used instead of the dichroic mirror 32, as illustrated in FIG. 3B. In this case, interference beams with wavelengths not longer than 0.9 µm (interference beams within the fourth wavelength range of the present invention) are inputted to the optical fiber FB37, interference beams with wavelengths longer than 0.9 µm and not longer than 1.2 µm (interference beams within the third wavelength range of the present invention) are inputted to the optical fiber FB39, and interference beams with wavelengths longer than 1.2 µm (interference beams within the fifth wavelength range of the present invention) are inputted to the optical fiber FB38.

Figure 3C:
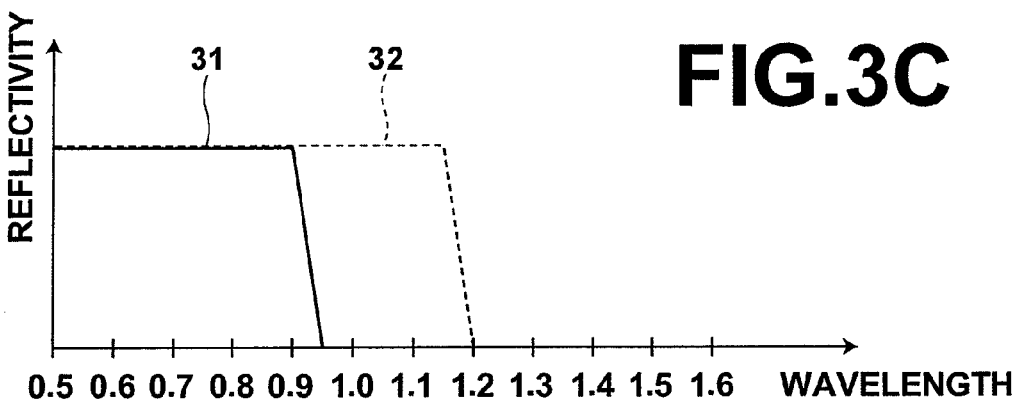
Figure 3D:
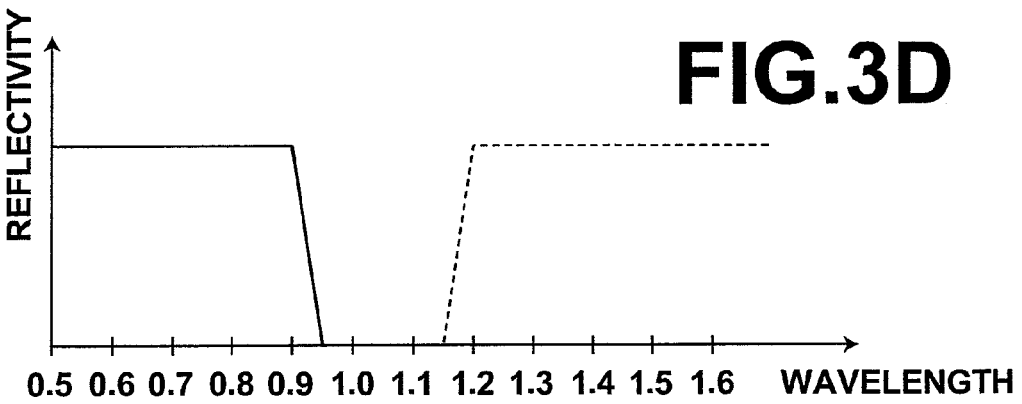

It is noted that the description has been and will be made using an example case in which light is divided such that the wavelength ranges do not overlap with each other in order to simplify the explanation. But strictly speaking, the divided wavelength ranges overlap with each other when the wavelength division is performed. For example, as illustrated in FIG. 3C, when the wavelength is divided using the dichroic mirror 31 that reflects light beams with wavelengths not longer than 0.9 µm nearly 100% and transmits light beams with wavelengths longer than 0.95 µm nearly 100%, and the dichroic mirror 32 that reflects light beams with wavelengths not longer than 1.15 µm nearly 100% and transmits light beams with wavelengths longer than 1.2 µm nearly 100%, interference beams with wavelengths not longer than 0.95 µm (interference beams within the fourth wavelength range of the present invention) within the interference beams L4a and L4b are inputted to the optical fiber FB37, interference beams with wavelengths longer than 0.9 µm and not longer than 1.2 µm (interference beams within the third wavelength range of the present invention) are inputted to the optical fiber FB38, and interference beams with wavelengths longer than 1.15 µm (interference beams within the fifth wavelength range of the present invention) are inputted to the optical fiber FB39. It is noted that, as illustrated in FIG. 3D, a dichroic mirror that transmits light beams with wavelengths not longer than 1.15 µm nearly 100% and reflects light beams with wavelengths longer than 1.2 µm nearly 100% may be used instead of the dichroic mirror 32 shown in FIG. 3C. In this case, interference beams with wavelengths not longer than 0.95 µm (interference beams within the fourth wavelength range of the present invention) are inputted to the optical fiber FB37, interference beams with wavelengths longer than 0.9 µm and not longer than 1.2 µm (interference beams within the third wavelength range of the present invention) are inputted to the optical fiber FB39, and interference beams with wavelengths longer than 1.15 µm (interference beams within the fifth wavelength range of the present invention) are inputted to the optical fiber FB38.

Optical fiber couplers 41a, 41b and 41c, for example, 2×2 optical fiber couplers with a branching ratio of 50:50, are connected to the optical fibers FB 37, FB38, and EB39, which divide the respective reference beams into halves and output to the interference beam detection means 40a, 40b, and 40c respectively. The interference beam detection means 40a, 40b, and 40c perform balanced detection to detect the halved interference beams using two light detection devices respectively. This structure reduces effects of fluctuations in the light intensity so that a clearer image may be obtained.

Figure 4A:
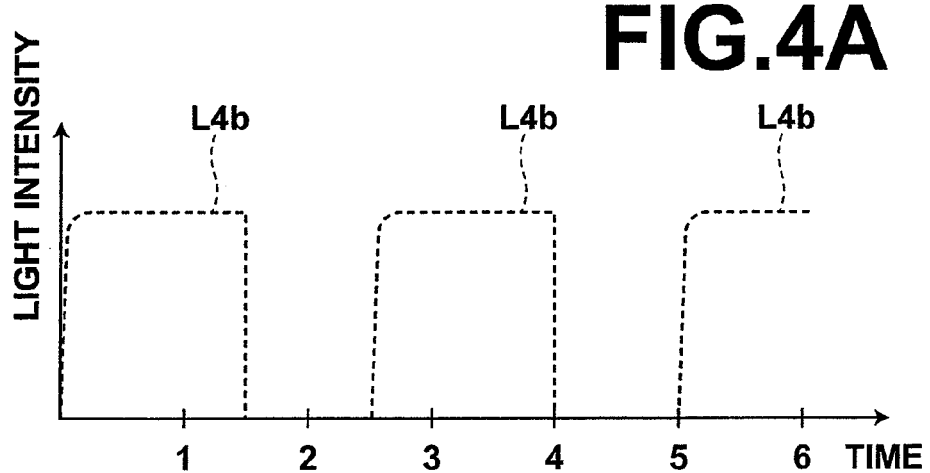
FIGS. 4A to 4C illustrate wavelength ranges detected by the interference beam detection means.
Figure 4B:
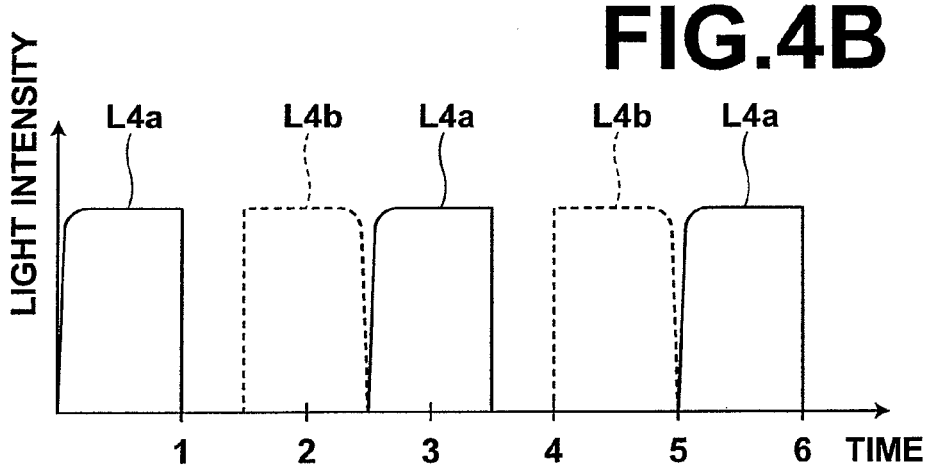
Figure 4C:
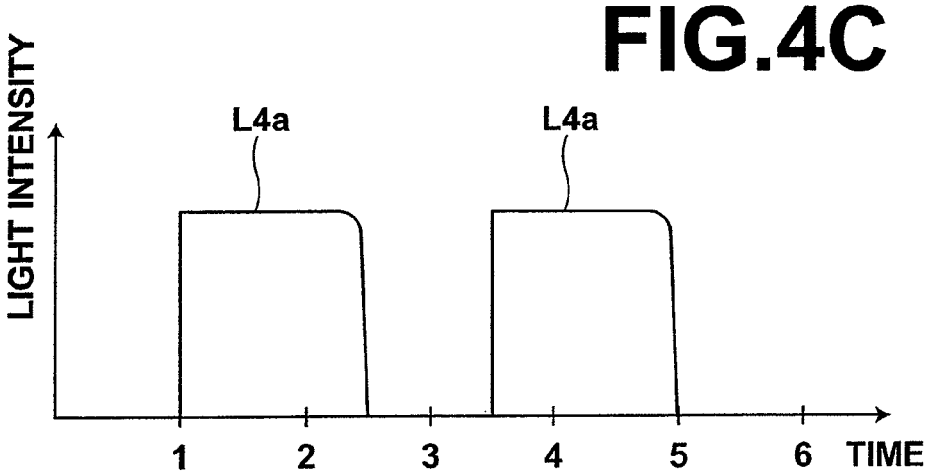

The interference beam detection means 40a, 40b, and 40c perform photoelectrical conversions on the respective interference beams and output to the tomographic image processing means 50. Here, the detection results in the interference beam detection means 40a, 40b, and 40c will be explained with reference to FIGS. 4A to 4C. FIGS. 4A to 4C illustrate changes in the intensity of the interference signals outputted from the interference beam detection means 40a, 40b, and 40c along the time axis. In order to facilitate understanding, each of the interference beams is broken down in the Figures. That is, the interference beam L4a is detected by the interference beam detection means 40b during a time period of 1 ms from the start of the sweep and by the interference beam detection means 40c during a time period from 1 to 2.5 ms after the start of the sweep. The interference beam L4b is detected by the interference beam detection means 40a during a time period of 1.5 ms from the start of the sweep and by the interference beam detection means 40b during a time period from 1.5 to 2.5 ms after the start of the sweep. It is noted that each of the interference beam detection means 40a, 40b, and 40c has a detection wavelength range which is wider than the wavelength range of the interference beam to be inputted.

The tomographic image processing means 50 includes a computer system, such as a personal computer, and the frequency versus time characteristic of each of the light beams La and Lb is stored in a not shown storage section in advance.

The tomographic image processing means 50 associates the detection results of the interference beam detection means 40a, 40b, and 40c with the oscillation frequencies of the wavelength swept light sources, and performs signal connections such that the detection results become equally frequency spaced interference signals to form a single broadband interference signal ISO. Then, the reflected light intensity of the measuring object S at each depth position is obtained by performing a frequency analysis, typically a Fourier transform, on the interference signal ISO.

An example operation of the optical tomographic imaging apparatus 100 will now be described with reference to FIGS. 1 to 4. The light beam La, swept in wavelength within the wavelength range $\Delta\lambda a$ (1.0 to 1.5 µs) at a constant period as shown in FIG. 2, is outputted from the light source 10a of the light source unit 10. The light beam La is propagated through the optical fiber FB1a and inputted to the beam combining means 2. Likewise, the light beam Lb, swept in wavelength within the wavelength range $\Delta\lambda b$ (0.6 to 1.1 µs) at a constant period as shown in FIG. 2, is outputted from the light source 10b. The light beam Lb is propagated through the optical fiber FB1b and inputted to the beam combining means 2. In the beam splitting means 3, the light beam La is split into the measuring light L1a and reference light L2a, and the light beam Lb is split into the measuring light L1b and reference light L2b.

The measuring beams L1a and L1b are propagated through the optical fiber FB32, inputted to port "a" of the circulator 4, outputted from port "b", propagated through the optical fiber FB 34, inputted to the probe 20 through the optical rotary connector 21, and irradiated onto the measuring object S. Then, the reflected beams L3a and L3b from the measuring object at each depth position "z" are inputted to the probe 20, propagated through the reverse path of the measuring beams, inputted to port "b" of the circulator 4, outputted from port "c", propagated through the optical fiber FB35, and inputted to the beam combining means 5.

The reference beams L2a and L2b split by the beam splitting means 3 are propagated through the optical fiber 33, and inputted to the beam combining means 5 after the optical path lengths thereof are controlled by the optical path length control means 6.

In the beam combining means 5, the reflected beams L3a and L3b are combined with the reference beam L2a and L2b respectively. The interference beam L4a produced when the reflected beam L3a is combined with the reference beam L2a, and the interference beam L4b produced when the reflected beam L3b is combined with the reference beam L2b are inputted to the wavelength dividing means 30.

Light beams with wavelengths not longer than 0.9 µm within the interference beams L4a and L4b outputted from the optical fiber FB36 and collimated by the lens 33 are reflected by the dichroic mirror 31, condensed by the lens 34, and inputted to the optical fiber FB37.

Light beams with wavelengths longer than 0.9 µm and not longer than 1.2 µm within the interference beams L4a and L4b are transmitted through the dichroic mirror 31, and reflected by the dichroic mirror 32, condensed by the lens 35, and inputted to the optical fiber FB38. Light beams with wavelengths longer than 1.2 µm are transmitted through the dichroic mirrors 31 and 32, condensed by the mirror 36, and inputted to the optical fiber 39.

The interference beams within the respective wavelength ranges are divided into halves by the optical fiber couplers 41a, 41b, and 41c and inputted to the interference detection means 40a, 40b, and 40c respectively. The interference detection means 40a, 40b, and 40c, perform balanced detection to detect the halved interference beams using two light detection devices respectively, perform photoelectrical conversions on the detected beams, and output to the tomographic image processing means 50 as interference signals.

As described above, the tomographic image processing means 50 associates the detection results of the interference beam detection means 40a, 40b, and 40c with the oscillation frequencies of the wavelength swept light sources, and performs signal connections such that the detection results become equally frequency spaced interference signals to form a single broadband interference signal ISO. Then, the light reflected intensity of the measuring object at each depth position is obtained by performing a frequency analysis, typically a Fourier transform, on the interference signal ISO.

The probe 20 is structured such that the fiber section on the distal side of the optical rotary connector 21 is rotated by a not shown motor to circularly scan the beams on the sample. Accordingly, after a beam reflected intensity at each depth position of a single point of the measuring object is obtained by the operation described above, by sequentially and slightly changing the irradiation positions of the measuring beams and obtaining a beam reflected intensity at each depth position in the same manner as described above, and integrating these beam reflected intensities, a two-dimensional optical tomographic image is generated. The generated tomographic image is displayed on the display unit 60 including a CRT (Cathode Ray Tube), a liquid crystal display, or the like.

As clear from the description, even the light beams La and Lb having wavelength regions partially overlapping with each other, are irradiated on the measuring object at the same time, the interference beams are obtained by dividing the interference beams L4a and L4b produced at that time into three wavelength ranges: a range not longer than 0.9 μm, a range from over 0.9 to 1.2 μm, and a range longer than 1.2 μm, so that interference signals corresponding to interference beams within the overlapped wavelength range may be obtained, thereby the measuring rate may be increased in comparison with the past and a higher resolution tomographic image may be obtained more rapidly.

Further, in the wavelength range from over 0.9 to 1.2 μm which includes an overlapped wavelength range between the wavelength range of the light beam La and the wavelength range of the light beam Lb, the light is outputted only from either the light source 10a or the light source 10b, so that even the light beams La and Lb are swept simultaneously and irradiated on the measuring object, the interference signal produced by the interference beam L4a and the interference signal produced by the interference beam L4b do not mixed together, that is, the interference signal produced by a first interference beam and the interference signal produced by a second interference beam may be obtained at the same time, so that the measuring rate may be increased in comparison with the past, and a higher resolution tomographic image may be obtained more rapidly.

Further, the use of the wavelength dividing means 30, having dichroic mirrors 31 and 32, allows division of interference beams in compact and efficient manner according to the wavelength.

In the present embodiment, the description has been made of a case in which the light beams La and Lb has wavelength ranges partially overlapping with each other, and the spectra of the interference beams L4a and L4b are regarded as continued. But the present invention is not limited to this. Where the spectra of the interference beams L4a and L4b are not regarded as continued, a tomographic image may be obtained by using, for example, a tomographic image processing means 55 shown in FIG. 5 instead of the tomographic image processing means 50.

Figure 5:
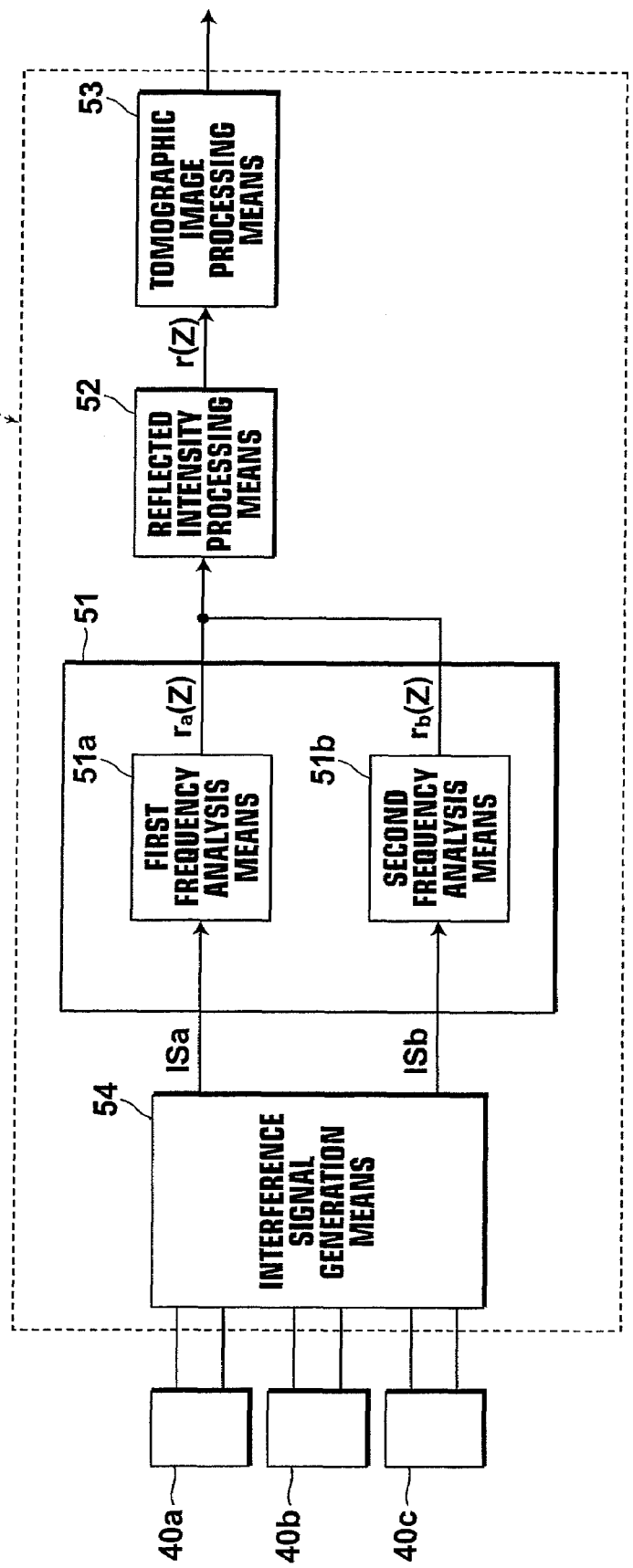
FIG. 5 illustrates an example of alternative embodiment of the tomographic image processing means.

The tomographic image processing means 55 includes a computer system, such as a personal computer. It has functions to generate an interference beam ISa corresponding to the interference beam L4a and an interference beam ISb corresponding to the interference beam L4b, to detect a plurality of intermediate reflected intensities (reflectivities) ra(z) and rb(z) at each dept position of the measuring object S by performing frequency analysis on the interference signals ISa and ISb, and to obtain a tomographic image of the measuring object S using the plurality of intermediate reflected intensities ra(z) and rb(z). More specifically, the tomographic image processing means 55 includes: an interference signal generation means 54 that generates the interference signals ISa and ISb from the detection results of the interference beam detection means 40a, 40b, and 40c; a frequency analysis means 51 that performs frequency analyses on the interference beams ISa and ISa to detect the intermediate reflected intensities ra(z) and rb(z) at each depth position; a reflected intensity processing means 52 that generates a reflected intensity r(z) from the plurality of intermediate reflected intensities ra(z) and rb(z) detected by the frequency analysis means 51; and a tomographic image generation means 53 that generates a tomographic image using the reflected intensity r(z) generated by the reflected intensity processing means 52, as illustrated in FIG. 5.

The interference signal generation means 54 includes a not shown storage section in which the frequency versus time characteristic of each of the light beams La and Lb is stored in advance, and generates the interference signals ISa and ISb based on the frequency versus time characteristic of each of the light beams La and Lb and detection results of each of the interference beam detection means 40a, 40b, and 40c. In the present embodiment, the interference signal ISa is generated by combining the detection results of the interference beam detection means 40b during a time period of 1 ms from the start of the sweep, and the detection results of the interference beam detection means 40c during a time period from 1 to 2.5 ms after the start of the sweep along the time axis. The interference signal ISb is generated by combining the detection results of the interference beam detection means 40a during a time period of 1.5 ms from the start of the sweep, and the detection results of the interference beam detection means 40b during a time period from 1.5 to 2.5 ms after the start of the sweep along the time axis.

The frequency analysis means 51 includes a first frequency analysis means 51a that performs a frequency analysis on the interference signal ISa to detect the intermediate reflected intensity ra(z) which bases on the light beam La, and a second frequency analysis means 51b that performs a frequency analysis on the interference signal ISb to detect the intermediate reflected intensity rb(z) which bases on the light beam Lb. Here, a method for calculating the intermediate reflected intensity (reflectivity) ra(z) in the first frequency analysis means 51 based on the interference signal ISa will be described briefly. For more detailed description, reference is made to the literature by M. Takeda, "Optical Frequency Scanning Interference Microscopes", Optical Engineering Contact, Vol. 41, No. 7, pp. 426-432, 2003.

Figure 6:
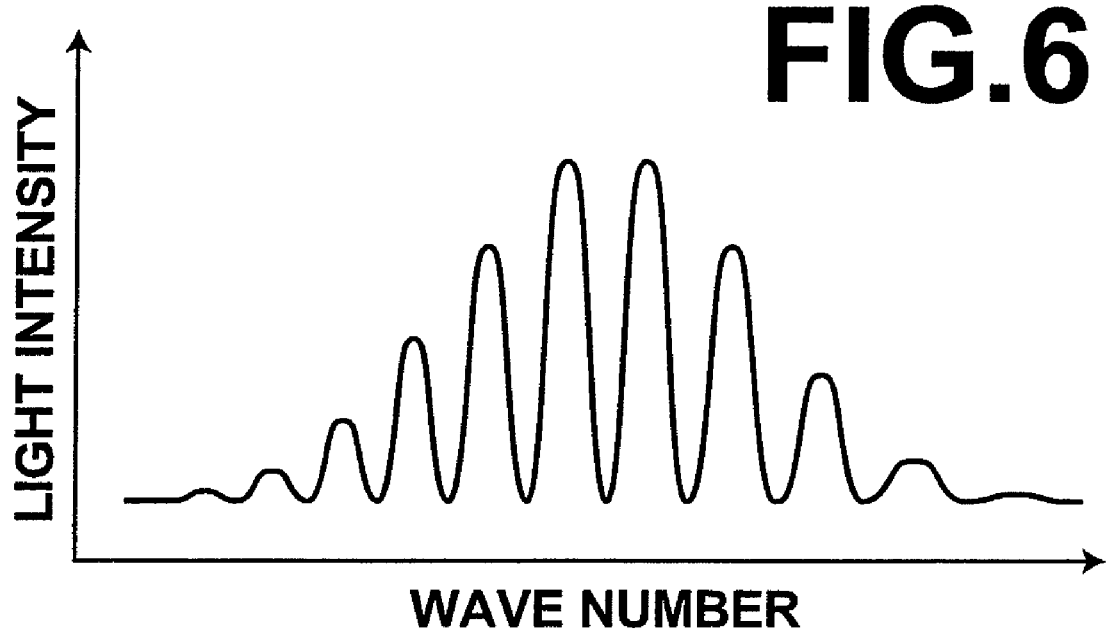
FIG. 6 is a graph illustrating an example of the interference beam detected by the interference beam detection means shown in FIG. 1.
Figure 7:
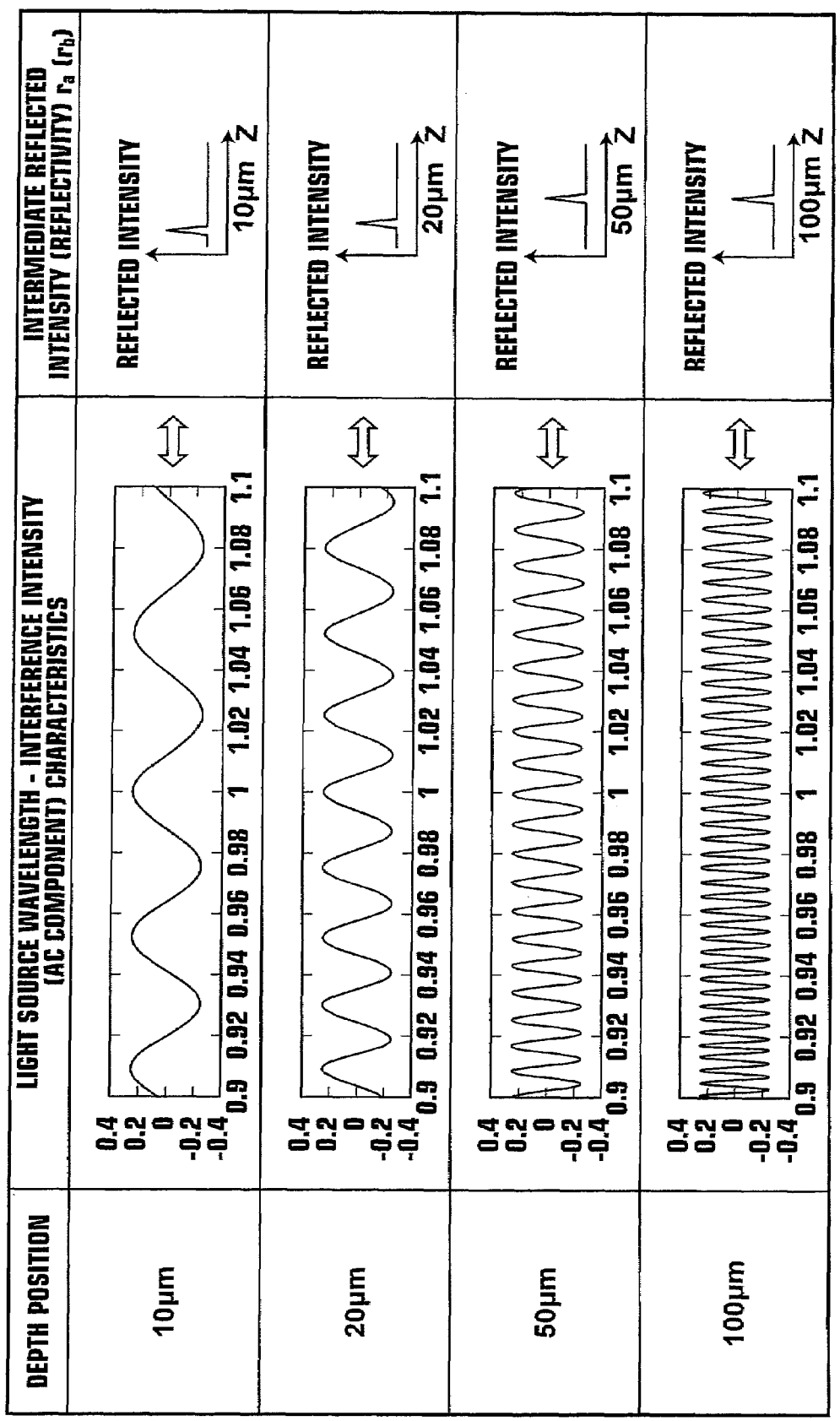
FIG. 7 illustrates reflected intensity at each depth position when frequency analysis is performed on the interference beam detected by the interference beam detection means shown in FIG. 1.

Assuming the light intensity of the interference pattern with respect to each optical path length difference l to be S(l) when the measuring beam L1a is irradiated onto the measuring object S, and reflected beam L3a from each depth of the measuring object interferes with the reference beam L2a with various optical path length differences (dept positions of the measuring object S), the light intensity I(k) detected by the interference beam detection means 40 may be expressed in the following and represented, for example, by the graph illustrated in FIG. 6.

$$I(k) = \int_0^\infty S(l)[1+\cos(kl)]dl \quad (1)$$

where, k is the wave number, l is the optical path length difference between the reference beam L2a and reflected beam L3a. Formula (1) above may be regarded as an interferogram in the optical frequency domain with the wave number k as a parameter. Accordingly, the light intensity S(l) of the interference signal ISa in each wavelength may be determined by performing, in the frequency analysis means 51a, a frequency analysis, through Fourier transform, on the spectral interference pattern detected by the interference beam detection means 40a, thereby the reflectivity at each depth position may be obtained, as illustrated in FIG. 7. Then, information of the distance from the measurement start position and the intermediate reflection intensity ra(z) are obtained. Likewise, the second frequency analysis means 51b obtains information of the distance from the measurement start position and the intermediate reflected intensity rb(z) for the interference signal ISb. That is, a plurality of intermediate reflected intensities ra(z) and rb(z) is obtained from the same beam-irradiated region of the measuring object S in the frequency analysis means 51. The frequency analysis means 51 may use any known spectral analysis technology such as, for example, maximum entropy measurement (MEM) or Yule-Walker method, other than the Fourier transform described above, for obtaining the intermediate reflected intensities ra(z) and rb(z).

The reflected intensity processing means 52 shown in FIG. 5 detects the reflected intensity r(z) used for generating a tomographic image from the plurality of intermediate reflected intensities ra(z) and rb(z) from each depth position "z" detected in the manner as described above. More specifically, the reflected intensity processing means 52 calculates the average value of the intermediate reflected intensities ra(z) and rb(z) at each depth position "z", r(z)=(ra(z)+rb(z))/2, as illustrated in FIG. 8.

The tomographic image generation means 53 generates a tomographic image using the reflected intensity r(z) detected by the reflected intensity processing means 52. More specifically, each of the measuring beams L1a and L1b is irradiated onto the measuring object S while it is scanned in the direction orthogonal to the depth direction "z" of the measuring object S. Then, reflected intensity r(z) with respect to each depth position at each of a plurality of measuring points is obtained by the tomographic image generation means 53. Then, the tomographic image generation means 53 generates a two- or three-dimensional tomographic image using the plurality of reflected intensities r(z) obtained at the respective measuring points.

In this way, noise component included in the reflectivities ra(z) and rb(z) are cancelled by calculating the average value of the plurality of intermediate reflected intensities ra (z) and rb (z) in the reflected intensity processing means 52 of the tomographic image processing means 50, thereby a high quality tomographic image may be obtained.

The absolute value of the reflected intensity at each depth position "z" of the measuring object S differs with the wavelength of the measuring beams L1a and L1b to be irradiated due to various factors, including light absorption/scattering properties of the measuring object S due to its composition. Since the plurality of measuring beams L1a and L1b is irradiated onto the same region of the measuring object S at the same time, a qualitative property, for example, peak positions where the reflected intensities become maximum, obtained from a certain depth "z1" approximately correspond with each other between the intermediate reflected intensities ra (z1) and rb(z1).

Consequently, even when the plurality of intermediate reflected intensities ra (z1) and rb (z1) have different values, noise components included in the respective reflected intensities may be cancelled and the component representing the tomographic information at the depth position "z1" may be emphasized by calculating the average value (r(za)) of the plurality of intermediate reflected intensities ra(z1) and rb(z1). In this way, even when a tomographic image is obtained using light beams La and Lb having different wavelength ranges instead of using a broadband light source, a high quality tomographic image may be obtained.

In the frequency analysis means 51, the sampling pitch with respect to the result of Fourier transform depends on the widths of the wavelength ranges $\Delta\lambda a$ and $\Delta\lambda b$ of the light beams La and Lb. Therefore, when the widths of the wavelength ranges $\Delta\lambda a$ and $\Delta\lambda b$ of the light beams La and Lb differ with each other as described above, the sampling pitches of the interference signals ISa and ISb differ with each other. In such a case, a value of "0" is inserted to the interference signal ISa obtained from the light beam La having a narrower wavelength range for the shortfall of the wavelength range to equalize the widths of the wavelength ranges $\Delta\lambda a$ and $\Delta\lambda b$.

Here, the description has been made of a case in which the average value of the intermediate reflected intensities ra (z) and rb(z) is calculated. Alternatively, the reflected intensity r(z) may be generated using the product of the intermediate reflected intensities ra(z) and rb(z). Then, strongest signal components of the intermediate reflected intensities ra(z) and rb(z9) are strengthened, so that the signal value of noise component is relatively reduced and a high quality tomographic image may be obtained. Further, various other methods may be used for generating the reflected intensity r(z) at each depth position using the intermediate reflected intensities ra(z) and rb(z), and obtaining a tomographic image. In the aforementioned embodiment, the description has been made of a case in which the reflected intensity is obtained using the average or product of the intermediate reflected intensities ra(z) and rb(z). But, by combining the ra(z) and rb (z) considering the wavelength ranges in which the interference signals ISa and ISb are obtained using spectral information of the light beams La and Lb outputted from the light source unit 10, the resolution of the reflected intensity r(z) may be increased. That is, ra(z) and rb(z) obtained by Fourier transform of the interference signals ISa and ISb, true reflected intensity r(z), and Fourier transforms ha(z) and hb(z) of the spectral shapes of the light beams La and Lb are in the following relationship.

$$ra(z)=r(z)\otimes ha(z) \quad (2)$$

$$rb(z)=r(z)\otimes hb(z) \quad (3)$$

⊗: denotes convolution operation

These may be deployed to ra=[ra(0), ra(1×dza), - - - ]$^T$, rb=[rb(0), rb(1×dzb), - - - ]$^T$, and r=[r(0), r(1×dz), - - - ]$^T$, and expressed in discrete representations, then $$Ha \cdot r = ra \quad (4)$$

$$Hb \cdot r = rb \quad (5)$$

where, Ha and Hb are matrices formed of each vector of ha=[ha(0), ha(1×dz), - - - ], and hb=[hb(0), hb(1×dz), - - - ] arranged by displacing the element thereof. Through a known technology, such as iteration method, the reflected intensity "r" may be obtained as the optimum solution of the relational expressions.

As described above, by calculating the reflected intensity r(z) from the relational expressions in consideration of the difference in the wavelength between the light beams La and Lb outputted from the light source unit 10, the reflected intensity r(z) may be calculated more accurately, thereby a high resolution tomographic image may be generated.

It is noted that the tomographic image processing means described above may also be used where the wavelength ranges of the light beams La and Lb are separated, or the like.

Figure 9:
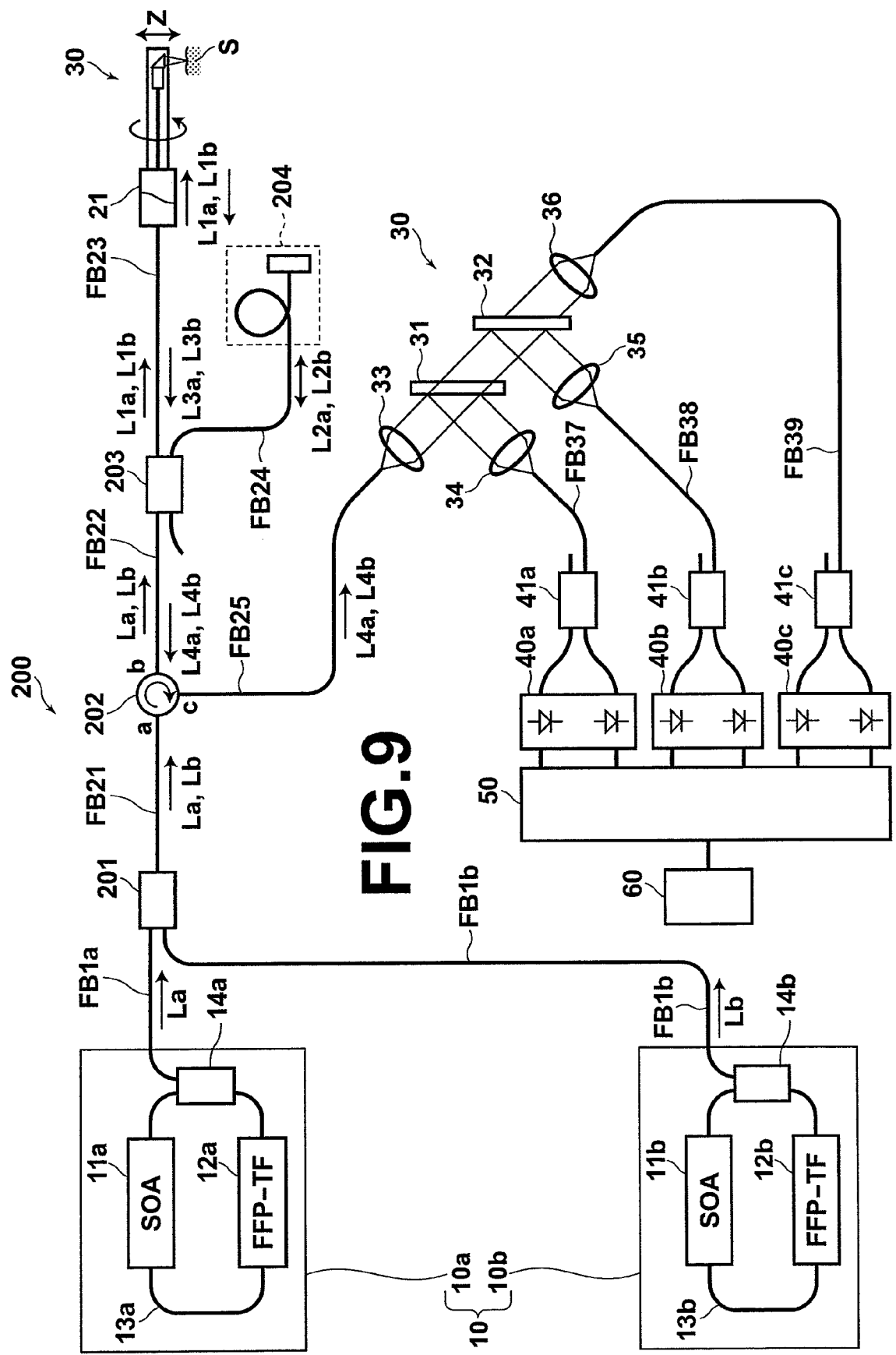
FIG. 9 is a schematic configuration diagram of the optical tomographic imaging apparatus according to a second embodiment of the present invention.

Next, an optical tomographic imaging apparatus 200 according to a second embodiment will be described with reference to FIG. 9. FIG. 9 is a schematic configuration diagram of the optical tomographic imaging apparatus 200. The optical tomographic imaging apparatus 200 is a SS-OCT system using a Michelson interferometer. In the optical tomographic imaging apparatus 200 in FIG. 9, components identical to those of the optical tomographic imaging apparatus of the previous embodiment are given the same reference symbols and will not elaborated upon further here.

In the optical tomographic imaging apparatus 200, the light beam La outputted from the light source 10a and guided by the optical fiber FB1a, and the light beam Lb outputted from the light source 10b and guided by the optical fiber FB1b are inputted to a beam combining means 201 and combined. The combined light beams La and Lb are guided through an optical fiber FB21 and inputted to port "a" of a circulator 202, outputted from port "b", propagated through an optical fiber FB22, and inputted to a beam combining/splitting means 203.

The beam combining/splitting means 203 includes, for example, a 2×2 optical coupler with a branching ratio of 90:10. It is noted that the beam combining/splitting means 203 of the present embodiment functions also as a beam combining means. The beam combining/splitting means 203 splits the light beams La and Lb into measuring beams L1a and L1b and reference beams L2a and L2b respectively in the ratio of 90% for the measuring beam and 10% for the reference beam, and outputs the measuring beams L1a and L1b on the side of an optical fiber FB23, and the reference beams L2a and L2b on the side of an optical fiber FB24.

The measuring beams L1a and L1b are inputted to the probe 20 through the optical rotary connector 21, guided through the probe 20, and irradiated onto the measuring object S. Then, the reflected beams L3a and L3b are inputted to the probe 20, propagated through the probe 20 and the optical fiber FB23, and inputted to the beam combining/splitting means 203.

In the mean time, the reference beams L2a and L2b are guided through the optical fiber 24 and inputted to the beam combining/splitting means 203 again after the optical path length thereof is changed by a reflective-type optical path length control means 204.

In the beam combining/splitting means 203, the reflected beams L3a and L3b are combined with the reference beams L2a and L2b. Then, an interference beam L4a is generated by the combination of the reflected beam L3a with the reference beam L2a, and an interference beam L4b is generated by the combination of the reflected beam L3b with the reference beam L2b. Here, it is noted that the combination of the reflected beam L3a with the reference beam L2b or the combination of the reflected beam L3b with the reference beam L2a does not produce any interference beam, since the light beams La and Lb are outputted from different light sources with each other.

The interference beams L4a and L4b are propagated through the optical fiber FB22, inputted to port "b" of the circulator 202, and outputted from port "c". Then, they are propagated through an optical fiber FB25 and inputted to the wavelength dividing means 30.

The structures and operations of the following wavelength dividing means 30, interference beam detection means 40a, 40b, and 40c, and tomographic image processing means 50 are identical to those of the first embodiment, so that they will not be elaborated upon further here.

In the first and second embodiments described above, a Si photodiode with an acceptable wavelength range of 320 to 1100 nm may be used for the light receiving element of the interference beam detection means 40a to which light beams with wavelengths in the wavelength range from 0.6 to 0.9 μm are inputted. For the light receiving element of the interference beam detection means 40b to which light beams with wavelengths in the wavelength range from 0.9 to 1.2 μm are inputted, or for the light receiving element of the interference beam detection means 40c to which light beams with wavelengths in the wavelength range from 1.2 to 1.5 μm are inputted, an InGaAs photodiode with an acceptable wavelength range of 900 to 1700 nm may be used.

Conventional apparatuses are structured such that the entire wavelength range of the light beam outputted from the light source unit needs to be covered by a single detector, and a usable photodiode for a light beam with the aforementioned wavelength ranges λa and λb has not been available. Thus, an apparatus capable of performing measurement using the combination of the wavelength ranges λa and λb has not been constructed. According to the optical tomographic imaging apparatuses of the present invention, however, a plurality of interference beam detection means is provided to enable detection with respect to each of the light beams, so that the measurement using the combination of the wavelength ranges λa and λb is allowed. Since the emission process of a semiconductor laser used for the light source and the light receiving process of a photodiode used for the photodetector are based on the same principle, so that a light beam within the emission band of a semiconductor laser made of a certain medium may be detected by a photodiode made of the same medium. Therefore, use of them as a pair allows the entire emission wavelength range to be covered and measured.

It is noted that the wavelength ranges of the optical tomographic imaging apparatuses of the present invention are not limited to those described above, and the wavelength ranges may be changed appropriately according to the composition of the measuring object S. For example, by combining a light beam in a wavelength range with small interaction with the measuring object (e.g., 1000 nm range less affected by water dispersion) and a light beam in a wavelength range with large interaction with the measuring object (e.g., 800 nm range), a high resolution tomographic image information may be obtained, and spectroscopic information of the measuring object, including absorption, dispersion, and fluorescence characteristic, and the like may be measured at the same time.

Where the optical tomographic imaging apparatus of the present invention is applied to an endoscope, if a light beam with a wavelength within a wavelength range which may be sensed by the CCD mounted in the endoscope, for example, a light beam with a center wavelength of 800 nm, is used as a light beam of a wavelength combined light source, the light beam may be used also as the aiming light, so that a separate aiming light source will not be required.

In the past, Fourier transform method in OCT measurement requires that the spectrum of the light source is continuous and broadband. Therefore, the light source unit 10 that outputs discrete light beams La and Lb has been though not to be suitable as the conventional OCT light source for obtaining a tomographic image.

As explained in the first embodiment of the present invention, however, it has been found that the use of the light source unit 10 that outputs a plurality of light beams La and Lb, each not having a broadband wavelength range but a different wavelength range with each other may provide a high resolution tomographic image. This may eliminate the necessity to use a specific light source that outputs a light beam having a continuous and broadband spectrum. Further, in the tomographic image processing means 55, a tomographic image is generated from the reflected intensities of two interference beams having different wavelengths, so that even the use of a discontinuous spectrum light source may provide a tomographic image without sidelobes, thereby a high resolution image may be obtained.

Further, the capability of obtaining a high resolution tomographic image by the use of a plurality of light beams having different wavelengths allows the selection between a high resolution type using many light beams and an inexpensive low resolution type using a fewer number of light beams, so that the measurement may be performed in response to the requirements.

Figure 10:
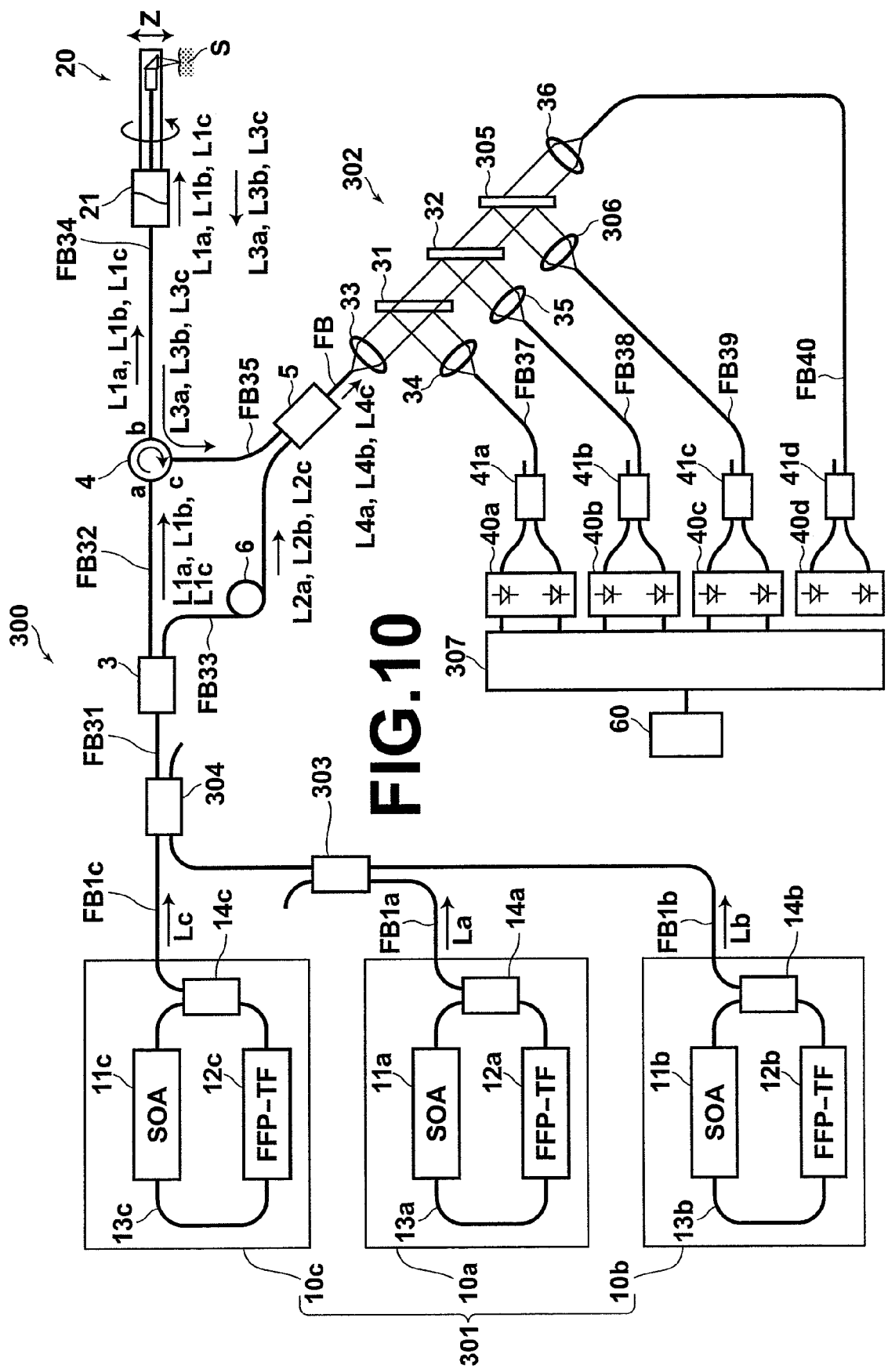
FIG. 10 is a schematic configuration diagram of the optical tomographic imaging apparatus according to a third embodiment of the present invention.
Figure 11:
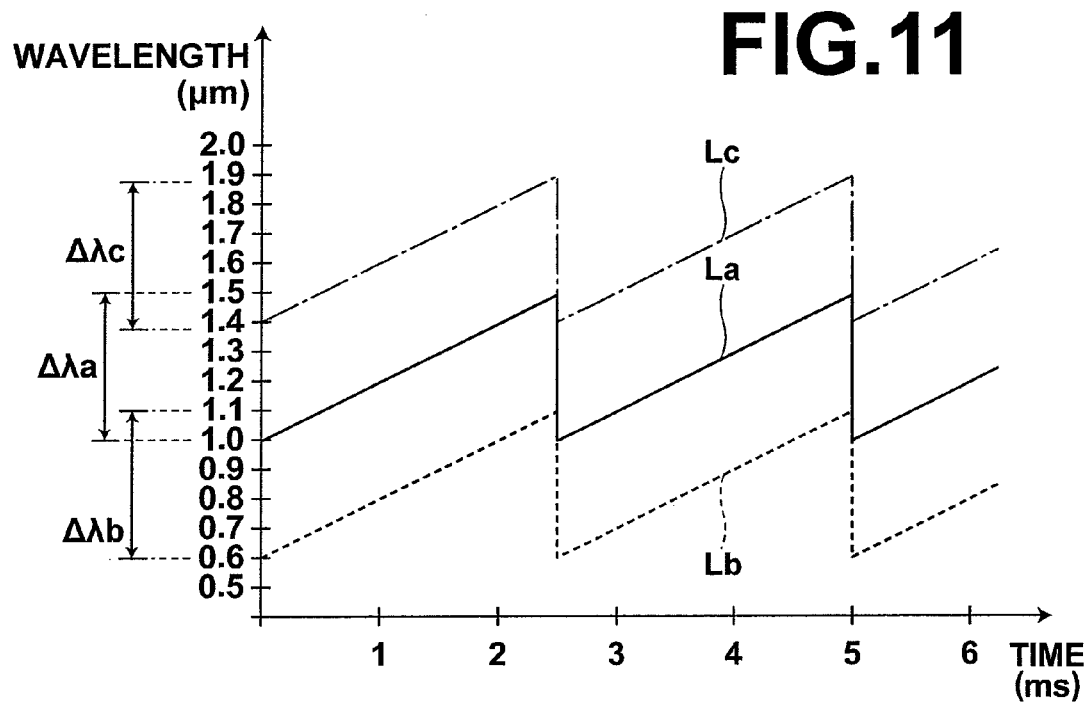
FIG. 11 illustrates wavelength sweep of the light source unit shown in FIG. 10.

Next, an optical tomographic imaging apparatus 300 according to a third embodiment will be described with reference to FIG. 10. FIG. 10 is a schematic configuration diagram of the optical tomographic imaging apparatus 300. The optical tomographic imaging apparatus 300 is a SS-OCT system using a Mach-Zehnder interferometer. The apparatus 300 obtains an optical tomographic image using three light beams. In the optical tomographic imaging apparatus 300 in FIG. 10, components identical to those of the optical tomographic imaging apparatus of the previous embodiment are given the same reference symbols and will not elaborated upon further here.

As illustrated in FIG. 10, the light source unit 301 of the optical tomographic imaging apparatus 300 includes: a light source 10a that outputs a laser beam La (swept wavelength range $\Delta\lambda a$: 1.0 to 1.5 μm); a light source 10b that outputs a laser beam Lb (swept wavelength range $\Delta\lambda b$: 0.6 to 1.1 μm); and a light source 10c that outputs a laser beam Lc (swept wavelength range $\Delta\lambda c$: 1.4 to 1.9 μm).

Figure 12:
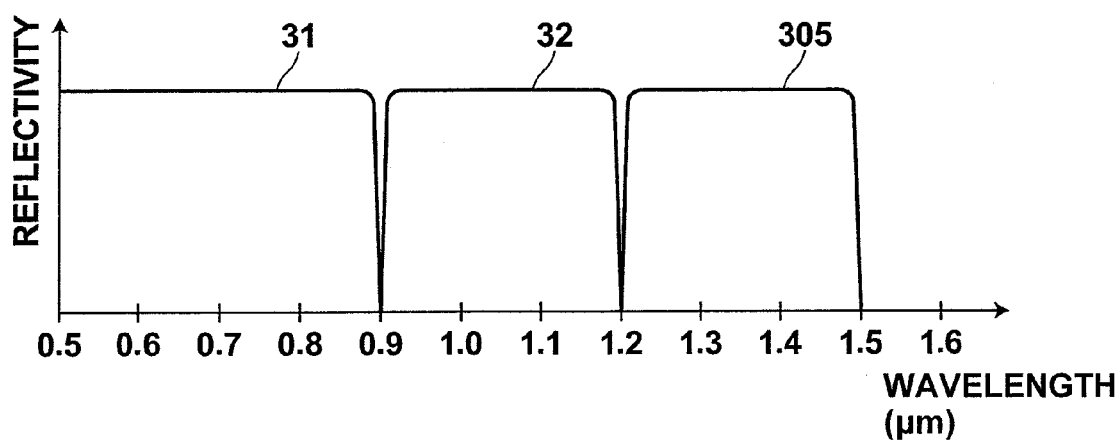
FIG. 12 illustrates wavelength reflection characteristic of the dichroic mirror shown in FIG. 10.
Figure 13A:
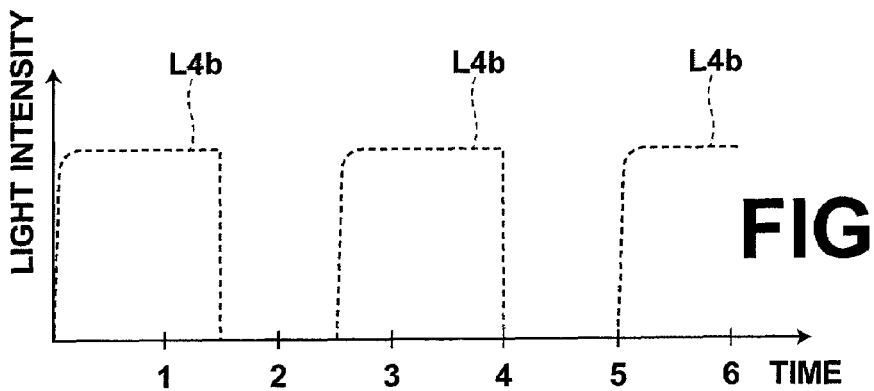
FIGS. 13A to 13D illustrate wavelength ranges detected by the interference beam detection means shown in FIG. 10.
Figure 13B:
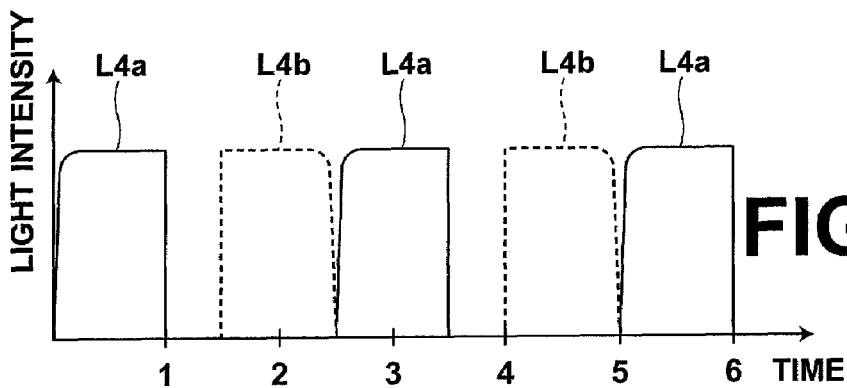
Figure 13C:
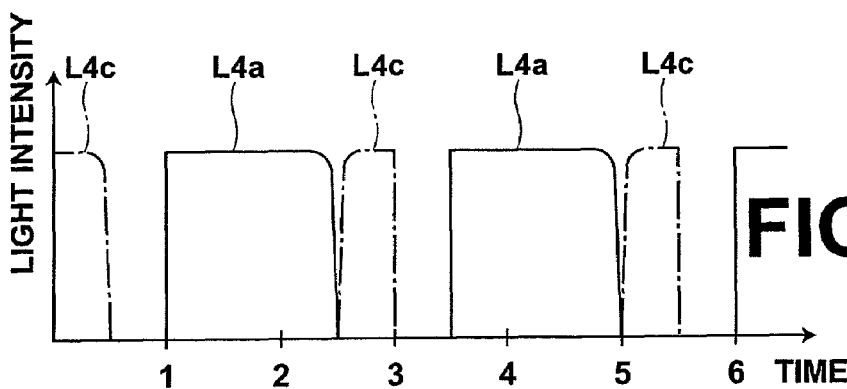
Figure 13D:
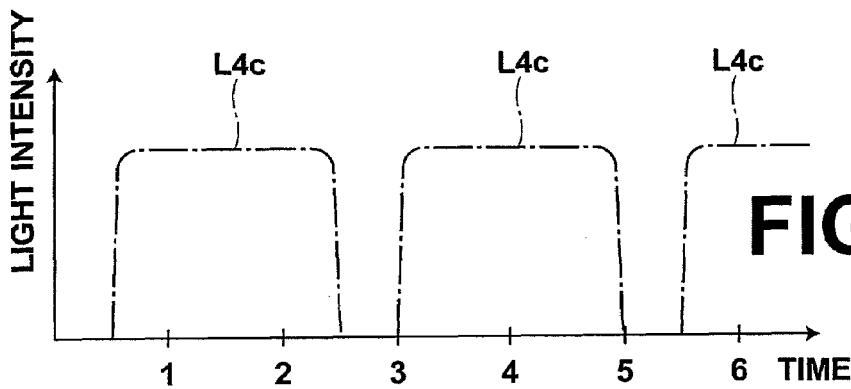

The wavelength dividing means 302 includes: the dichroic mirror 31 that reflects light beams with wavelengths not longer than 0.9 μm and transmits light beams with wavelengths longer than 0.9 μm; the dichroic mirror 32 that reflects light beams with wavelengths not shorter than 0.9 μm and not longer than 1.2 μm and transmits light beams having other wavelengths; a dichroic mirror 305 that reflects light beams with wavelengths not shorter than 1.2 μm and not longer than 1.5 μm and transmits light beams having other wavelengths; and the lenses 33 to 36 and a lens 306. The wavelength reflection characteristic of each of the dichroic mirrors is shown in FIG. 12.

The light beams La, Lb, and Lc are propagated through the optical fibers FB1a, FB1b, and FB1c respectively, and combined by beam combining means 303 and 304. Then, in the beam splitting means 3, the light beams La, Lb, and Lc are split into the measuring beam L1a and reference beam L2a, measuring beam L1b and reference beam L2b, and measuring beam L1c and reference beam L2c respectively.

Thereafter, as in the optical tomographic imaging apparatus 100 shown in FIG. 1, the measuring beams L1a, L1b, and L1c are propagated through the optical fiber FB32, inputted to port "a" of the circulator 4, outputted from port "b", propagated through the optical fiber FB34, inputted to the probe 20 through the optical rotary connector 21, and irradiated onto the measuring object S from the probe 20. Then, the reflected beams L3a, L3b, and L3c from the measuring object at each depth position "z" are inputted to the probe 20, propagated through the reverse path of the measuring beams, inputted to port "b" of the circulator 4, outputted from port "c", propagated through the optical fiber FB35, and inputted to the beam combining means 5.

In the beam combining means 5, the reflected beams L3a, L3b, and L3c are combined with the reference beams L2a, L2b, and L2c respectively. The interference beam L4a produced when the reflected beam L3a is combined with the reference beam L2a, the interference beam L4b produced when the reflected beam L3b is combined with the reference beam L2b, and the interference beam L4c produced when the reflected beam L3c is combined with the reference beam L2c are inputted to the wavelength dividing means 302. Light beams with wavelengths not longer than 0.9 μm within the interference beams L4a, L4b, and L4c are inputted to the optical fiber FB37. Light beams with wavelengths longer than 0.9 μm and not longer than 1.2 μm are inputted to the optical fiber FB38, light beams with wavelengths longer than 1.2 μm and not longer than 1.5 μm are inputted to the optical fiber FB39, and light beams with wavelengths longer than 1.5 μm are inputted to the optical fiber FB40.

The interference beams in the respective wavelength ranges are divided into halves by the optical fiber couplers 41a, 41b, 41c and 41d and inputted to the interference beam detection means 40a, 40b, 40c, and 40d respectively. The interference detection means 40a, 40b, 40c, and 40d perform balanced detection to detect the halved interference beams using two light detection devices respectively, perform photoelectrical conversions on the detected beams, and output to the tomographic image processing means 307. FIGS. 13A to 13D illustrate changes in the intensity of the interference signals outputted from the interference beam detection means 40a, 40b, 40c, and 40d along the time axis. In order to facilitate understanding, each of the interference beams is broken down in the Figures.

The tomographic image processing means 307 includes a computer system, such as a personal computer, and the frequency versus time characteristic of each of the light beams La, Lb, and Lc is stored in a not shown storage section in advance. The tomographic image processing means 307 associates the detection results of the interference beam detection means 40a, 40b, 40c, and 40d with the oscillation frequencies of the wavelength swept light sources, and performs signal connections such that the detection results become equally frequency spaced interference signals to form a single broadband interference signal ISO. Then, the light reflected intensity of the measuring object S at each depth position is obtained by performing a frequency analysis, typically a Fourier transform, on the interference signal ISO.

In the optical tomographic imaging apparatus 300, the reflected beam intensity at each depth position of each point on a circle of the measuring object S is obtained while rotating the fiber section on the distal side of the optical rotary connector 21 and scanning the measuring beams circularly on the sample, as in the optical tomographic imaging apparatus 100 according to the first embodiment shown in FIG. 1. The tomographic image processing means 307 generates a two-dimensional optical tomographic image by integrating the reflected beam intensities at the respective depth positions of the respective points on the measuring object S, and the generated optical tomographic image is displayed on the display unit 60 including a CRT, a liquid crystal display, or the like.

In the optical tomographic imaging apparatus 300 shown in FIG. 10, three light beams are used, but a greater number of light beams may be used. Where "n" light beams are used, the number of interference beam detection means required is n+1.

Figure 14:
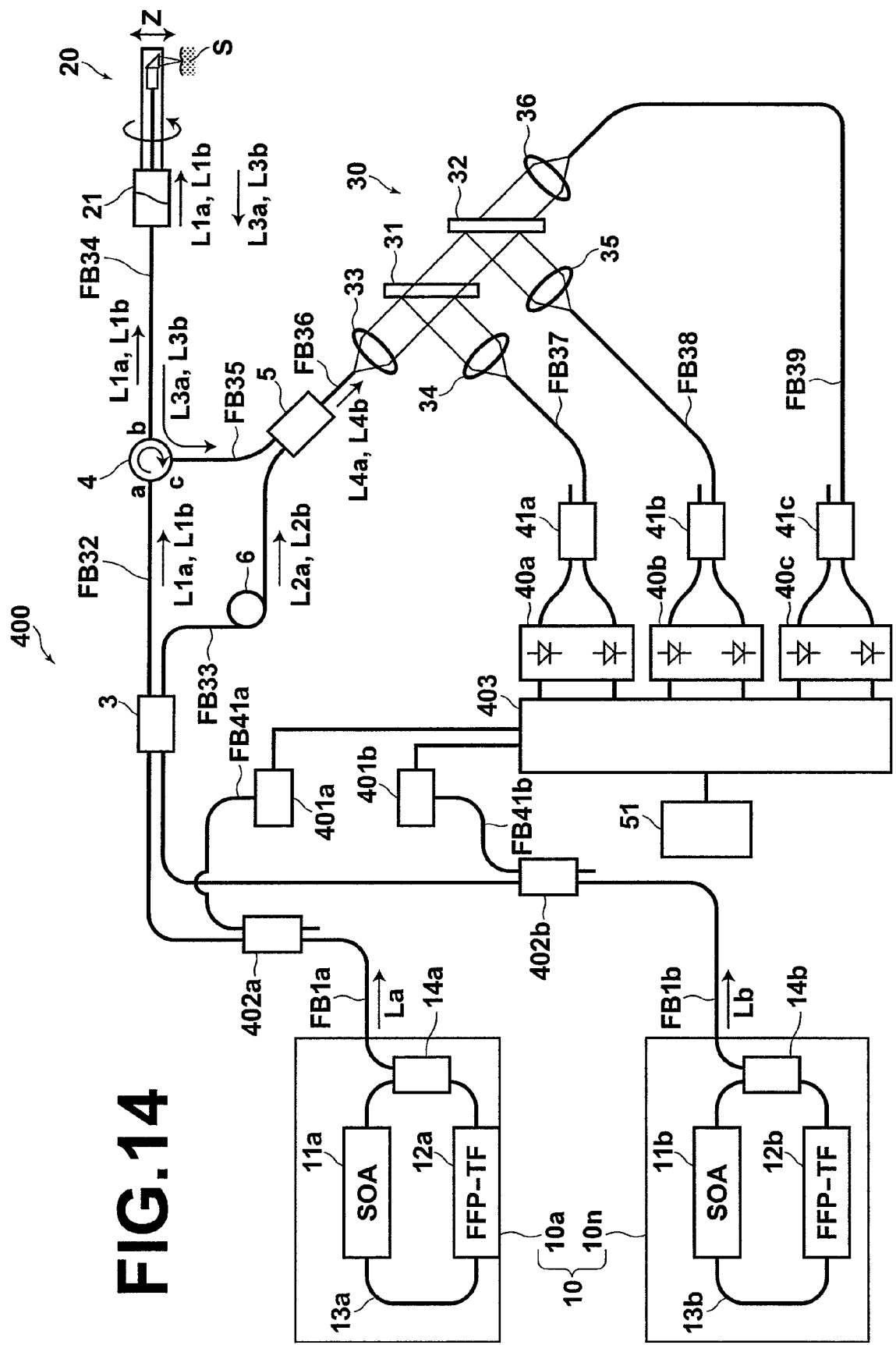
FIG. 14 is a schematic configuration diagram of the optical tomographic imaging apparatus according to a fourth embodiment of the present invention.

Next, an optical tomographic imaging apparatus 400 according to a fourth embodiment will be described with reference to FIG. 14. FIG. 14 is a schematic configuration diagram of the optical tomographic imaging apparatus 400. The optical tomographic imaging apparatus 400 is a SS-OCT system using a Mach-Zehnder interferometer. The apparatus 400 includes frequency versus time characteristic detection means 401$a$ and 401$b$ that detect frequency versus time characteristic of each of the light beams La and Lb respectively and obtains an optical tomographic image using the frequency versus time characteristic of each of the light beams La and Lb detected by each of the frequency versus time characteristic detection means 401$a$ and 401$b$. In the optical tomographic imaging apparatus 400 shown in FIG. 14, components identical to those of the optical tomographic imaging apparatus of the previous embodiment are given the same reference symbols and will not elaborated upon further here.

A portion of the light beam La outputted from the light source 10$a$ is branched to an optical fiber FB41$a$ by a branching means 402$a$ and inputted to the frequency versus time characteristic detection means 401$a$. Likewise, a portion of the light beam Lb outputted from the light source 10$b$ is branched to an optical fiber FB41$b$ by a branching means 402$b$ and inputted to the frequency versus time characteristic detection means 401$b$. Each of the frequency versus time characteristic detection means 401$a$ and 401$b$ includes, for example, a Fabry-Perot interferometer, and detects the frequency versus time characteristic of each of the light beams La and Lb in real time.

A tomographic image processing means 403 associates the detection results of the interference beam detection means 40$a$, 40$b$, and 40$c$ with the frequency versus time characteristic of each of the light beams La and Lb detected by the frequency versus time characteristic detection means 401$a$ and 401$b$, and performs signal connections such that the detection results become equally frequency spaced interference signals to form a single broadband interference signal ISO. Then, the reflected light intensity of the measuring object S at each depth position is obtained by performing a frequency analysis, typically a Fourier transform, on the interference signal ISO.

As described above, an optical tomographic image is generated using the frequency versus time characteristic of each of the light beams La and Lb, so that the frequency versus time characteristic of each of the light beams La and Lb needs not be stored in the tomographic image processing means in advance. Further, matching of the frequency versus time characteristic of each of the light beams La and Lb with a frequency versus time characteristic stored in advance is not required, so that the wavelength ranges, sweep speed, sweep timing, or the like of the light beams La and Lb may be changed according to the measuring object S, which improve the usefulness of the apparatus.

In the first, third, and fourth embodiments, the description has been made using an SS-OCT employing a Mach-Zehnder interferometer as an example, while in the second embodiment the description has been made using an SS-OCT employing a Michelson interferometer. But each embodiment may use any type of interferometer as long as embodied as a SS-OCT. For example, a Fizeau interferometer may also be used.

In each of the embodiments, the description has been made of a case in which a plurality of fiber ring type wavelength swept light sources is used as the light source unit. But other types of wavelength swept light sources may also be used. For example, a wavelength swept light source that uses a diffraction grating, polygon, bandpass filter, or the like as the wavelength selection means, and a rare-earth doped optical fiber, or the like as the gain medium may also be used.

Figure 15:
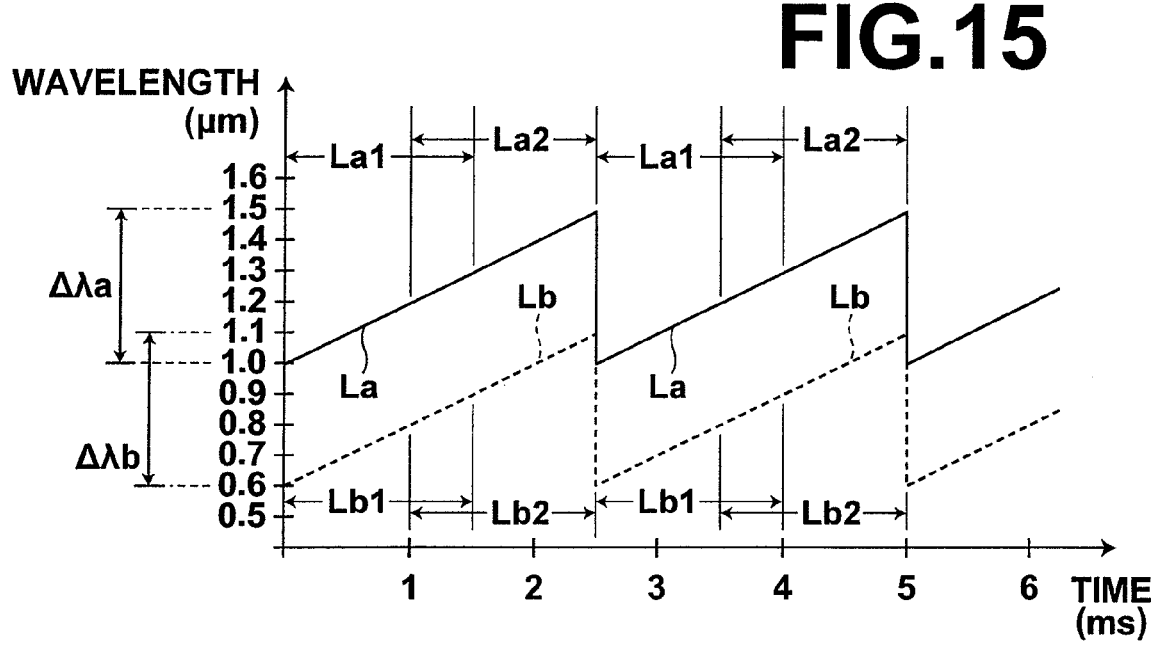
FIG. 15 illustrates wavelength sweep of the light source unit of an alternative embodiment.

Further, such a structure may be employed in which the light sources described in Japanese Unexamined Patent Publication No. 2006-047264 and U.S. Pat. No. 6,665,320 are used as a pair, and a plurality of light source pairs is combined. For example, as illustrated in FIG. 15, the light source for each light beam may be formed by combining a wavelength swept laser that outputs a light beam on the short wavelength side and a wavelength swept laser that outputs a light beam on the long wavelength side. That is, the light beam La may be formed by combining a light beam La1 outputted from a wavelength swept laser that sweeps the wavelength within the wavelength range from 1.0 to 1.3 μm and a light beam La2 outputted from a wavelength swept laser that sweeps the wavelength within the wavelength range from 1.2 to 1.5 μm while oscillating them in synchronization with each other within the overlapping wavelength range, and the light beam Lb may be formed by combining a light beam Lb1 outputted from a wavelength swept laser that sweeps the wavelength within the wavelength range from 0.6 to 0.9 μm and a light beam Lb2 outputted from a wavelength swept laser that sweeps the wavelength within the wavelength range from 0.8 to 1.1 μm while oscillating them in synchronization with each other within the overlapping wavelength range. Where the oscillations take place in synchronization with each other within the overlapping wavelength range, the light beams La and Lb may be formed by combining light beams outputted from three or more wavelength swept light sources.

Still further, in each of the embodiments, the description has been made of a case in which a single light beam is outputted from a single gain medium. But a multi-color light source that outputs a plurality of light beams having different wavelengths from a single gain medium may be used. In this case, for example, the light source unit 10 may be replaced with the multi-color light source.

The swept wavelength range of a single light beam is not limited to the example range describe above, but needs to be greater than a predetermined wavelength range. There are no specific boundary values for the predetermined wavelength range, but if a system with a resolution less than in the order of approximately 1 mm is envisioned, it is in the order of approximately more than several tens of GHz in terms of the frequency band of the light.

Further, in each of the embodiments, the description has been made of a case in which the light beams are guided through optical fibers, and combined or split by optical couplers or WDM couplers. Alternatively, a bulk optical system may be employed in which beam combining and splitting is performed spatially using a mirror, prism, dichroic mirror, dichroic prism, or the like. Instead of the optical fiber probe, a galvanomirror may be used to scan the spatially propagating beam.

In the second to fourth embodiments, each light beam outputted from the light source unit may have a discrete wavelength range, as in the first embodiment.

Further, in each of the embodiments, the description has been made of a case in which reflected beam from a measuring object or back scattered light is measured. Where the measuring object is a transparent medium, such as a glass block, transparent film, or the like, and the in-plane refractive index distribution, thickness distribution, birefringence, or the like is obtained, transmitted beam is measured instead of reflected beam. In such a case, the transmitted beam may be guided to the beam combining means, instead of reflected beam, and combined with the reference beam. Here, the other structures and methods described in each of the embodiments may be applied as they are.

What is claimed is:

1. An optical tomographic imaging apparatus, comprising:
a light source unit having a first light source that outputs a
first light beam which is swept in wavelength repeatedly within a first wavelength range, and a second light source that outputs a second light beam which is swept in wavelength repeatedly within a second wavelength range which is different in range from the first wavelength range, in which a part of the wavelength sweep of the first light beam and a part of the wavelength sweep of the second light beam are performed at the same time;

a beam splitting means that splits the first and second light beams into first measuring and reference beams, and second measuring and reference beams respectively;

a beam combining means that combines first and second reflected beams, which are the reflected beams from a measuring object when the first and second measuring beams are irradiated on the measuring object, with the first and second reference beams respectively;

a wavelength dividing means that divides a first interference beam produced when the first reflected beam is combined with the first reference beam by the beam combining means and a second interference beam produced when the second reflected beam is combined with the second reference beam by the beam combining means into at least a third wavelength range which includes a portion of the first wavelength range and a portion of the second wavelength range, a fourth wavelength range which is shifted on the short wavelength side of the third wavelength range, and a fifth wavelength range which is shifted on the long wavelength side of the third wavelength range;

a first interference beam detection means that detects an interference beam within the third wavelength range as a first interference signal, a second interference beam detection means that detects an interference beam within the fourth wavelength range as a second interference signal, and a third interference beam detection means that detects an interference beam within the fifth wavelength range as a third interference signal; and a tomographic image processing means that generates a tomographic image of the measuring object using the first, second, and third interference signals detected by the first, second, and third interference beam detection means respectively.

2. The optical tomographic imaging apparatus of claim 1, wherein:
the first and second wavelength ranges include an overlapping wavelength range where the wavelength ranges overlap with each other at an end portion thereof on either the long wavelength side or the short wavelength side;
the third wavelength range includes the entire portion of the overlapping wavelength range; and
a light beam with a wavelength within the third wavelength range is outputted only from either one of the first and second light sources while light beams with wavelengths within the third wavelength range are outputted from the either one of the light sources.

3. The optical tomographic imaging apparatus of claim 1, wherein the wavelength dividing means is formed of two dichroic mirrors.

4. The optical tomographic imaging apparatus of claim 2, wherein the wavelength dividing means is formed of two dichroic mirrors.

5. The optical tomographic imaging apparatus of claim 1, wherein:
the apparatus includes a frequency versus time characteristic detection means that detects a frequency versus time characteristic of each of the first and second light beams and outputs to the tomographic image processing means; and
the tomographic image processing means is a means that generates the tomographic image using the frequency versus time characteristic of each of the first and second light beams detected by the frequency versus time characteristic detection means.

6. The optical tomographic imaging apparatus of claim 2, wherein:
the apparatus includes a frequency versus time characteristic detection means that detects a frequency versus time characteristic of each of the first and second light beams and outputs to the tomographic image processing means; and
the tomographic image processing means is a means that generates the tomographic image using the frequency versus time characteristic of each of the first and second light beams detected by the frequency versus time characteristic detection means.

7. The optical tomographic imaging apparatus of claim 3, wherein:
the apparatus includes a frequency versus time characteristic detection means that detects a frequency versus time characteristic of each of the first and second light beams and outputs to the tomographic image processing means; and
the tomographic image processing means is a means that generates the tomographic image using the frequency versus time characteristic of each of the first and second light beams detected by the frequency versus time characteristic detection means.

8. The optical tomographic imaging apparatus of claim 4, wherein:
the apparatus includes a frequency versus time characteristic detection means that detects a frequency versus time characteristic of each of the first and second light beams and outputs to the tomographic image processing means; and
the tomographic image processing means is a means that generates the tomographic image using the frequency versus time characteristic of each of the first and second light beams detected by the frequency versus time characteristic detection means.

* * * * *